United States Patent [19]

Hermon-Taylor et al.

[11] Patent Number: 4,948,723

[45] Date of Patent: Aug. 14, 1990

[54] METHOD OF DIAGNOSIS AND SEVERITY-ASSESSMENT OF PANCREATIC DISEASE

[75] Inventors: John Hermon-Taylor; Brian M. Austen, both of London, England

[73] Assignee: Bioscience International, Inc., Boston, Mass.

[21] Appl. No.: 78,737

[22] Filed: Jul. 28, 1987

Related U.S. Application Data

[63] Continuation-in-part of Ser. No. 3,738, Jan. 6, 1987.

[51] Int. Cl.$^5$ .................. G01N 33/53; G01N 33/543; C07K 7/06; C07K 17/00

[52] U.S. Cl. .......................................... 435/7; 435/28; 436/518; 436/528; 436/533; 436/548; 436/811; 436/813; 530/327; 530/328; 530/329; 530/812

[58] Field of Search ................... 435/7, 28, 177, 180; 436/518, 536, 544, 548, 811, 528, 533, 531, 813, 501, 804, 823; 530/327, 328, 329, 387, 330, 335, 812, 815

[56] References Cited

U.S. PATENT DOCUMENTS 4,503,143  3/1985  Gerber et al. ...................... 436/510

OTHER PUBLICATIONS

Hermon-Taylor et al., Clinica Chimica Acta, vol. 109, 1981, pp. 203-209.
Terry et al., Clinica Chimica Acta, vol. 150, 1985, pp. 151-163.
Grataroli et al., Biochimie, vol. 63, 1981, pp. 677-684.
Eskola et al., Clin. Chem., vol. 29/10, 1983, pp. 1777-1780.
Sternby et al., Biochimica et Biophysica Acta, vol. 789, 1984, pp. 164-169.
Neralainen et al., Clin. Chem., vol. 31/7, 1985, pp. 1116-1120.
Geokas et al., The Journal of Biological Chemistry, vol. 252, No. 1, 1977, pp. 61-67.
Hermon-Taylor et al., Scand. J. Gastroenterol [Supp:] 1985, vol. 117, pp. 39-46.
Guy et al., Biochemistry, vol. 17, No. 9, 1978, pp. 1169-1675.
Sternby et al., Biochimica et Biophysica Acta, vol. 786, 1984, pp. 109-112.
Grataroli et al., Eur. J. Biochem., vol. 122, 1982, pp. 111-117.
Largman et al., Biochimica et Biophysica Acta, vol. 623, 1980, pp. 208-212.
Davis et al., (1955), J. Bio. Chem., 212:515-529.
Eskola et al., (1988), Clin. Chem., 34:1052-1054.
Gudgeon et al., (1988), Pancreas, 3:598.
Gudgeon et al., Pacreas (1988) 3:599.
Hurley et al., (1988), J. Immunological Methods, 111:195-203.
Msoero et al., (1982), Dig. Dis. Sci., 27:1089-1094.
Rinderknecht, 1988), Int. J. Pancreatology, 3:105-112.
Steinberg et al., Dig. Dis. Sci., (1984), 29:988-993.
Walsh, (1970) Methods in Enzymology 19:41-62.
Grant et al., (1979), Biochem. Piophys. Acta., 567:207-215.
Magee et al., (1981), Biochem. J. 197:239-244.
Grant et al., (1983), Gut 24 (1):16-19.
Talbot et al., (1984) Digestive Diseases and Sciences 29(11):1009-1014.
Grant et al., (1984) Clinica Chmica Acta 142:39-45.
Cliffe et al., in "Proceedings of the 8th American Peptide Symposium", 1983, edited by Kruby and Rich (Pierce Chemical Company, Ill.), pp. 611-614.
Cliffe et al., (1985), Int. J. Peptide Protein Res. 25:663-672.

*Primary Examiner*—Robert J. Warden
*Assistant Examiner*—Florina B. Hoffer
*Attorney, Agent, or Firm*—Irell & Manella

[57] ABSTRACT

Pancreatic disease can be diagnosed by assaying a patient's body fluid, e.g. serum or urine, for the activation peptides of pancreatic zymogens specifically cleaved by proteolysis during activation, (PAP) e.g. peptides including the sequence $D_4K$ having the lysine as the carboxy terminus. When PAP is assayed for, the test provides a means for distinguishing necrotising acute pancreatitis from oedematous acute pancreatitis, provides for diagnosis of chronic pancreatitis in exacerbation, and permits monitoring of the severity progress of the disease. Also described are antibodies having specificity for the pancreatic activation peptides, as well as such peptides and antibodies which are labelled with revealing agents and/or immobilized on solid supports, and their use in diagnostic test kits.

10 Claims, 12 Drawing Sheets

ELUTION PROFILES OF ANTI-$D_4K$ ANTISERA FROM RABBITS 2 AND 17 AFTER AFFINITY CHROMATOGRAPHY ON IMMOBILISED $D_4K$, SHOWING THE PRESENCE OF $Ca^{2+}$ DEPENDENT AND $Ca^{2+}$ INDEPENDENT ANTIBODIES.

DISPLACEMENT BY SYNTHETIC PEPTIDES OF $^{125}$I-LABELLED YD$_4$K BOUND TO SPECIFIC ANTISERA.

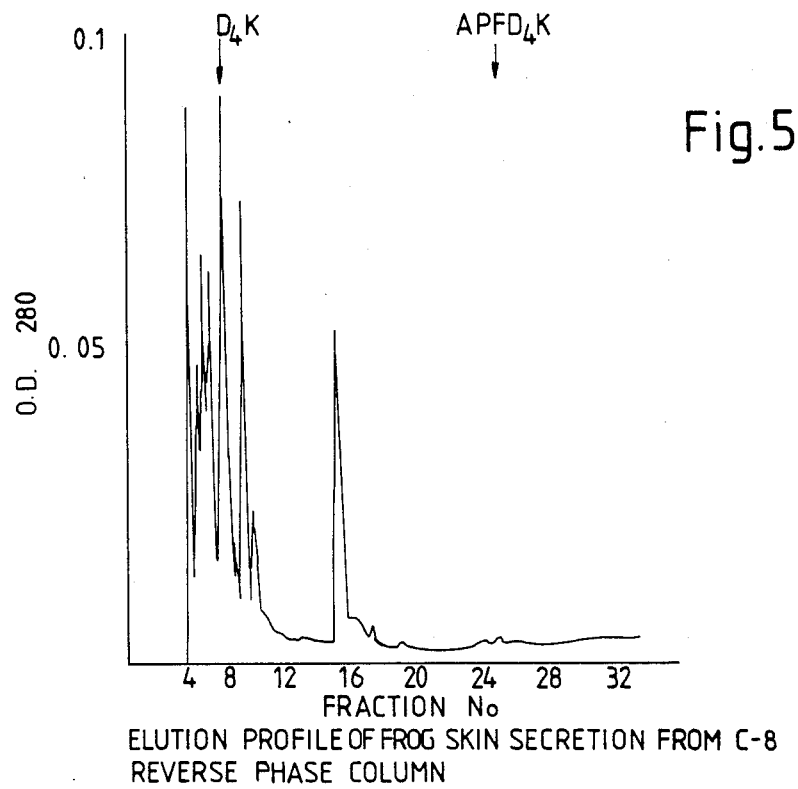
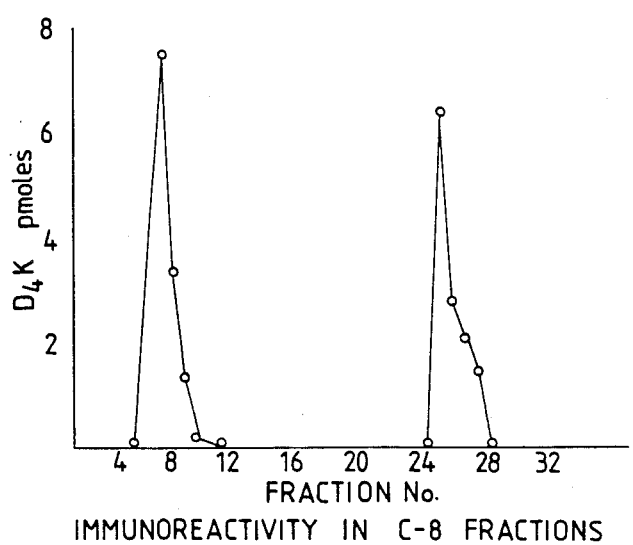
Fig.5
ELUTION PROFILE OF FROG SKIN SECRETION FROM C-8 REVERSE PHASE COLUMN
IMMUNOREACTIVITY IN C-8 FRACTIONS

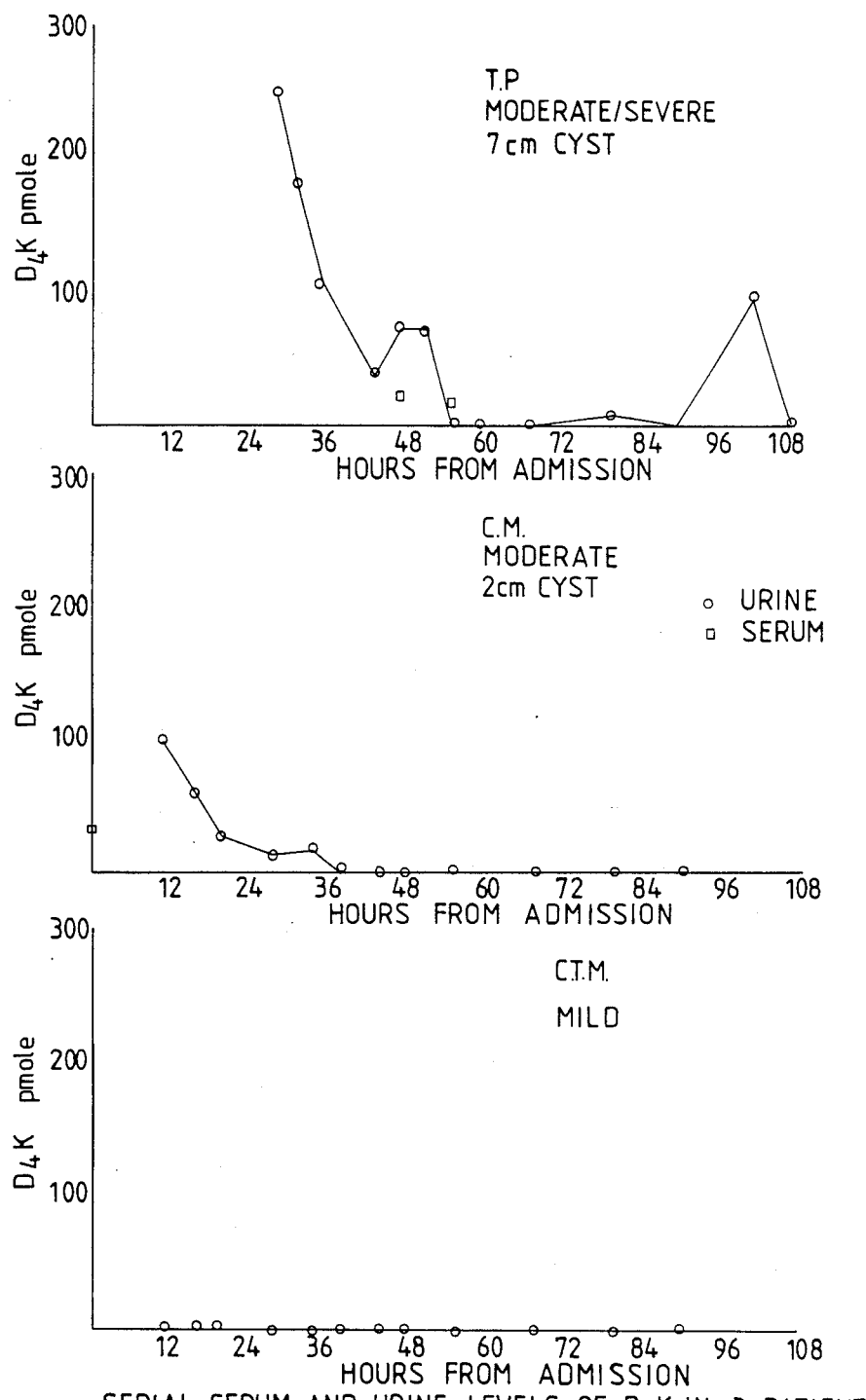
Fig.12 SERIAL SERUM AND URINE LEVELS OF $D_4K$ IN 3 PATIENTS ADMITTED WITH ACUTE PANCREATITIS

METHOD OF DIAGNOSIS AND SEVERITY-ASSESSMENT OF PANCREATIC DISEASE

CROSS REFERENCE TO RELATED APPLICATIONS

This Application is a continuation-in-part of our application Ser. No. 003,728 filed Jan. 16th 1987.

TECHNICAL FIELD

The present invention relates generally to the diagnosis of pancreatic disease. More particularly, the present invention relates to trypsinogen activation peptides and their use in diagnosing pancreatitis.

BACKGROUND OF THE INVENTION

Acute and chronic pancreatitis are human diseases which have shown a significant increase in frequency in recent years [1]. Acute pancreatitis presents as an abdominal emergency, whereas chronic pancreatitis in general involves the differential diagnosis of chronic or intermittent abdominal pain.

The exocrine pancreas produces and stores a range of digestive enzymes, including amylase and lipase, biosynthesised in active form, and others including trypsinogens, chymotrypsinogens, proelastases, procarboxypeptidases, and prophospholipases A2, synthesised as inactive proenzymes or zymogens. Zymogen activation normally occurs following secretion of pancreatic juice into the duodenal lumen, and involves the specific catalytic conversion of trypsinogen to active trypsin by duodenal enteropeptidase (E.C. 3.4.21.9). This removes from trypsinogen an amino-terminal oligopeptide containing the sequence tetra-L-aspartyl-L-lysine, an event followed by tryptic activation of the other proenzymes in a cascade of proteolytic cleavage. Activation peptides of pancreatic zymogens released in the course of this physiological process are thought to be degraded by duodenal oligopeptidases.

Acute pancreatitis is characterised by two distinct clinicopathological types [2]. In acute oedematous pancreatitis, pancreatic acinar cell damage is accompanied by leakage of inactive digestive zymogens with active amylase and lipase into the peritoneal cavity and circulation. The active enzymes are identifiable in the resulting ascitic fluid as well as in blood and urine, while proteinase digestive zymogens and prophospholipase remain unactivated. Although local inflammation and fat necroses due to active lipase occur, the condition is generally non-lethal and recovers within a few days of conservative management. In acute necrotising pancreatitis on the other hand, pancreatic acinar cell damage and digestive enzyme release is associated with varying degrees of digestive zymogen activation. Although complexes form between pancreatic proteinases and circulating macromolecular inhibitors, some of these complexes remain catalytically active. Phospholipase A2 is also active in plasma. Widespread local and disseminated multiorgan damage results in a high morbidity and mortality.

The biochemical diagnosis of acute pancreatitis has traditionally relied on the detection in plasma, serum, urine, or ascitic fluid, of pancreatic digestive enzymes or their zymogens released from the pancreas itself as a result of the disease. The quantitation of total amylase activity in serum has been the principle diagnostic test employed [reviewed in ref. 3]. The arrival of sensitive immunological methods permitted the development of assays for pancreatic proteolytic enzymes and their zymogens including trypsin and trypsinogens [4-18], elastase [19,20], chymotrypsin [21], phospholipase [22,23], carboxypeptidases [24] and, in addition, lipase [25,26] and pancreatic trypsin inhibitor [27,28]. Some of these immunoassays particularly those using polyclonal antisera were complicated by the variable proteolytic degradation of their target molecules. Additional problems with these assays arise due to steric inhibition of antibody binding to target enzymes in complexes with macromolecular inhibitors [29,30]. Furthermore antibody recognising both parent zymogen and active enzyme is unable to distinguish between the two.

Amylase assays were improved to differentiate between pancreatic isoamylase and amylase activity contributed by other organs, particularly salivary glands [31-33]. Simultaneous detailed assessment of many of these tests in multiple patients with acute pancreatitis has, however, shown that the detection of lipase or immunoreactive trypsinogen does not improve initial diagnostic accuracy over the measurement of pancreatic isoamylase alone, and does not permit the biochemical recognition of the severe acute necrotising disease [34]. Amylase estimation in the diagnosis of pancreatic disease is complicated by sporadic cases of hyperamylasaemia, the need to distinguish pancreatic from other sources of amylase, the variable degradation of amylase activity in association with severe acute pancreatitis, and the inability to equate serum amylase levels with the severity of pancreatitis or to identify the onset of necrosis. Serum amylase estimations may also be unreliable in the recognition of ethanol-induced pancreatitis [35-37]. Attempts to improve the accuracy of severity prediction by assay for catalytically active pancreatic phospholipase A2 may prove a more fruitful approach [38]. This however is likely to have difficulties with specificity since phospholipases A2 are present in macrophages, granulocytes, platelets and other cells [39] and are elevated in blood in other acute abdominal conditions and septic shock [40].

The principal clinical diagnostic difficulty in acute pancreatitis therefore has been to distinguish severe abdominal pain with hyperamylasemia due to oedematous pancreatitis, from the ore serious necrotising form in the earliest hours of the disease when intensive treatment, the use of specific enzyme inhibitors, and even surgical intervention and subtotal resection, may be life saving.

In chronic pancreatitis the diagnostic problem is different since subacute or intermittent abdominal pain due to chronic pancreatitis may not be associated with hyperamylasemia and distinction is required from the many other potential causes of such symptoms.

THE INVENTION

The present invention is based upon the specific assay in body fluids for free pancreatic activation peptides PAP (the activation peptides of pancreatic zymogens specifically cleaved by limited proteolysis during activation) having available carboxy-termini. Such an assay will, for the first time, provide a precise method for recognising and quantifying pancreatic zymogen activation. Our invention is based on our appreciation that different forms of pancreatitis are associated with the specific release, or otherwise, of PAP. This general method will distinguish between forms of pancreatitis occurring with or without zymogen activation and will be clinically applicable to the dignosis, severity prediction, and disease-course-monitoring in acute pancreatitis. It will also provide a precise diagnostic test for chronic pancreatitis in exacerbation.

BRIEF DESCRIPTION OF THE FIGURES

FIG. 5 depicts the elution profile of frog skin secretion from C-8 reverse phase column and the immunoreactivity in C-8 fractions.

FIG. 12 demonstrates serial serum and urine levels of D$_4$K in three patients presenting with acute pancreatitis.

DETAILED DESCRIPTION

Figure 1:
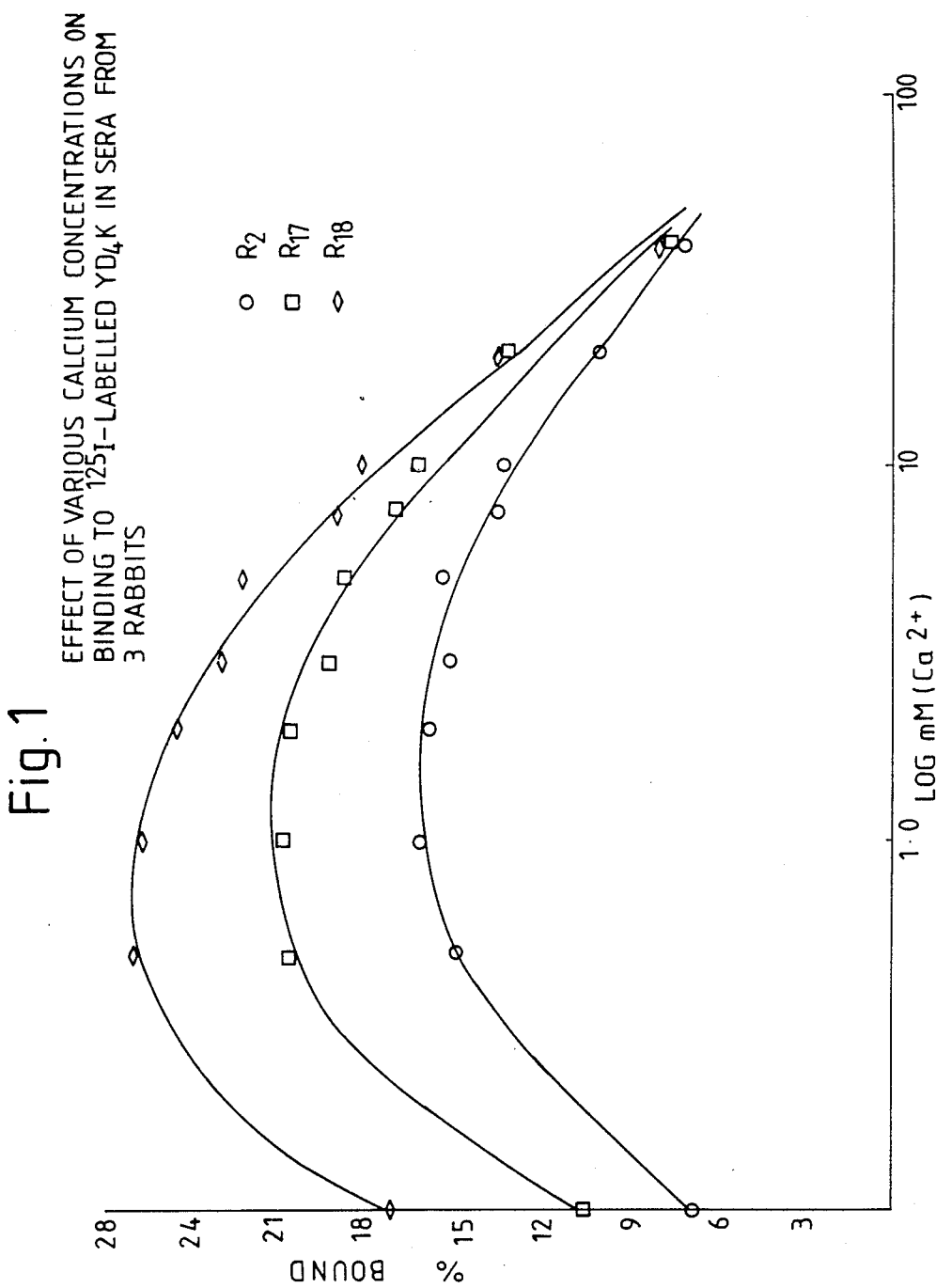
FIG. 1 depicts the effect of various calcium concentrations on binding to $^{125}$I-labeled YD$_4$K in sera from three rabbits.

In the test, a sample of the patient's body fluid particularly blood plasma, serum, urine or ascites will be assayed for one or more PAP. PAP available for such a strategy include the tetra-L-aspartyl-L-lysine (D$_4$K in the single letter amino acid code used in relation to this and subsequently mentioned PAP) containing trypsinogen activation peptides (TAP) in which the D$_4$K sequence is itself resistant to pancreatic proteolysis. Other suitable activation peptides are DSGISPR [41] the activation peptide of human pancreatic prophospholipase A$_2$ (PLAP) and the APGPR [42] activation peptide of procolipase (CLAP). In addition proelastase I and II activation peptides [43] or derivatives of their limited proteolysis, as well as the large (90–100 amino acid) amino terminal moiety cleaved from procarboxypeptidases A and B, may also be considered. Of particular importance in this invention is the strategy of using antibody specifically carboxy-terminally directed against PAP. This will ensure that antibody binding and a positive result in the assay will only be reported when zymogen activation by limited proteolysis has indeed occurred, and that zymogens themselves in which PAP are linked by their carboxy-termini, will not be recognised.

EXAMPLES

Immunoassay of Trypsinogen Activation Peptides (TAP)

In the following description, reference is frequently made to the immunoassay of trypsinogen activation peptides TAP. This is but one example of PAP and what is described in the following description in relation to TAP applies equally to the other PAP described above and below. When reference is made to TAP this is not to imply that the TAP that will be present will necessarily only be the pentapeptide D$_4$K itself since additional amino terminal amino acid residues may be present. These differ among trypsinogen isoenzymes or may have been modified by amino terminal degradation. The TAP peptides recognised in the assay will include the D$_4$K sequence at the carboxy-terminus and it is the D$_4$K sequence that is to be recognised.

The activation peptides of trypsinogens are highly conserved in vertebrate evolution and contain the polyanionic sequence D$_4$K upstream of the lysyl-isoleucyl target bond that is cleaved during specific proteolytic activation [44,45]. The assay of the sample for the amino acid sequence D$_4$K is most satisfactorily carried out using an antibody that recognises the D$_4$K sequence with specificity for C-terminal D$_4$K peptides and such antibodies form a further aspect of the present invention. These antibodies may be polyclonal or monoclonal. The polyclonal antibodies of the invention can be raised in animals by conventional techniques using as the immunogen D$_4$K or D$_4$K having a short leader sequence, e.g. alanyl-prolyl-phenylalanyl with or without cysteine at the amino terminus and either as free D$_4$K containing peptide or D$_4$K peptide haptenised prior to use as an immunogen. Where haptenisation is required, the D$_4$K sequence or peptides including it can be chemically bonded to conventional peptide haptens such as bovine serum albumin (BSA) or thyroglobulin (TG).

When monoclonal antibodies are required, they may be prepared by conventional hybridoma technology, again using D$_4$K or an amino acid sequence including D$_4$K or D$_4$K haptenised prior to use as the immunogen. Monoclonal antibodies to D$_4$K may also be generated by using D$_4$K bound to previously prepared anti-D$_4$K antibody as the immunogen.

The present invention is based upon our appreciation that assay of PAP such as the D$_4$K sequence can provide valuable unambiguous information concerning the existence and nature of pancreatic disorders in a patient. The exact way in which the assay is carried out is not critical and use may be made of any of the available direct or indirect (competitive) assays as well as two-site sandwich assays and assays involving quantification of antibody occupancy. The assay will normally involve the formation, in samples where D$_4$K peptides are present, of a conjugate between the peptide including the D$_4$K sequence and the antibody, said conjugate carrying a revealing label and being formed either in the solid phase or in the liquid phase of a solid/liquid phase reaction mixture, separating the solid phase from the liquid phase and determining the presence of or amount of the revealing label in either the solid phase or the liquid phase as a measure of the presence of or amount of, respectively, peptide including the D$_4$K sequence in the sample. Competitive assays normally require the attachment of the revealing label to competing $D_4K$ hut labelling of a second anti-$D_4K$ antibody is necessary for the two-site sandwich assay. Any of the conventional revealing labels can be used, enzyme labels or radioactive labels being preferred although immunofluorescence can also be used. The selection of the enzyme or radioactive label may be $^{125}I$, one of the preferred radioactive labels, while horseradish peroxidase or alkaline phosphatase are the preferred enzymes. Biotin may also be used. Polyclonal or monoclonal anti-$D_4K$ carrying a revealing label form a further aspect of the present invention as does the pentapeptide $D_4K$ having a revealing label directly attached to one of its constituent amino acids and polypeptides including the labelled pentapeptide conjugated to another polypeptide. Amplification methods may be employed such as those which link alkaline phosphatase coupled to $D_4K$ peptide into the conversion of $NADP^+$ to $NAD^+$. The $NAD^+$ so formed then catalytically activities and $NAD^+$-specific redox cycle yielding an intensely coloured formazan dye [46].

The anti-$D_4K$ can be used, in accordance with the present invention, in conventional radio-immunoassays, in enzyme-linked or enzyme-multiplied immunoassays, in accordance with developed techniques, or in alternative immunoassays employing chemiluminescence, bioluminescence, photon emission fluorometry, electroluminescence, polarisation fluorescence, time resolved or other techniques. These would form the basis of reference laboratory immunoassays or simplified methods applicable to use in satellite laboratory, physicians office, emergency department, ward or intensive care unit. These methods frequently require the anti-$D_4K$ antibody or $D_4K$ itself to be immobilised by attachment to an inert solid substrate, such as latex particles or polystyrene balls or powder which can be packed into a column through which the test solutions can be run and such immobilised polyclonal or monoclonal anti-$D_4K$ and immobilised peptides comprising the $D_4K$ sequence having the lysine (K) as the carboxy terminus, with or without the attachment of a revealing label, form further aspects of the invention.

The invention also provides diagnostic test kits. Such kits comprise, as one component the labelled peptide of the invention (alone or conjugated to another peptide) or the labelled antibody of the invention. Alternatively, the test kit is one comprising a solid and a liquid component where the solid component is an immobilised peptide or antibody of the invention and one of the components is labelled, preferably with an enzyme or radioactive label.

In general, assays in accordance with the present invention using immobilised anti-$D_4K$ will include the step of bringing a liquid sample, suspected of including $D_4K$ peptides, into contact with a solid phase including a polyclonal or monoclonal anti-$D_4K$ in competition with $D_4K$ carrying a revealing agent, and assaying either the solid phase or the liquid phase for the presence of $D_4K$ carrying the revealing agent and taking the presence of that conjugate as a measure of the $D_4K$ content of the sample. Assays in accordance with the present invention will also include the method of bringing a liquid sample suspected of including $D_4K$ peptides, into contact with a solid phase with attached polyclonal or monoclonal anti-$D_4K$, separating the solid from the liquid phase, and quantifying the $D_4K$ bound by immobilised anti-$D_4K$, using a monoclonal second anti-$D_4K$ antibody carrying a revealing agent. An alternative method may also be used of quantifying antibody or immobilised $D_4K$ peptide occupancy in one or two dimensions on solid phase after exposure to the test sample, by the subsequent use of $D_4K$ peptides or antibody coupled to a revealing agent. Assays in accordance with the present invention will also include the method of adding anti-$D_4K$ polyclonal or monoclonal antibody with or without revealing agent, to the sample to be tested and bringing the treated sample into contact with $D_4K$ peptides immobilised on solid phase either directly or via an intermediate and such immobilised $D_4K$ peptide forms part of the present invention. $D_4K$ peptides on membranes or other solid phase support may be in the form of a disc which may have a central well, ring, or minicolumn. The test will be read by the intensity and/or distribution of anti-$D_4K$ binding to the immobilised $D_4K$ using the attached revealing agent or a revealing agent coupled to a second antibody to anti-$D_4K$ Ig. Assays in accordance with the present invention will also include the method of bringing the sample suspected of including $D_4K$ peptides into contact with a complex comprising anti-$D_4K$ antibody and $D_4K$, immobilised on an inert solid support and with or without a revealing agent. If the $D_4K$ is directly bound to the support, the antibody carries any revealing agent and vice versa. The displacement of initial $D_4K$ from the solid phase by $D_4K$ peptides in the sample may then be quantified.

The assay of the present invention may also be used to monitor the severity progress of pancreatitis. To do this, samples of body fluid are removed from the patient on at least two separate occasions spaced apart from one another by one to four hours and each sample is assayed for the concentration of $D_4K$ peptide. By taking several samples from the patient over a 24 hour period, it is possible to determine whether the severity of the patient's condition is changing and is such as to require surgery or other specific treatment.

The $D_4K$ peptides and other PAP are also of value in that they can be used for the purification, by affinity chromatography, of polyclonal or monoclonal anti-$D_4K$ or other anti-PAP. In such purification procedures, the $D_4K$ peptide or other PAP will normally be immobilised in a sterically accessible manner, on a solid support such as polystyrene or a polysaccharide such as a polydextran, a liquid sample containing relatively impure anti-$D_4K$ or other anti-PAP brought into contact with the imobilised $D_4K$ peptide or other PAP forming a $D_4K$/anti-$D_4K$ or other PAP/anti-PAP conjugate on the support. After washing the solid phase the anti-$D_4K$ or other anti-PAP is eluted to give a solution containing a relatively more pure form of anti-$D_4K$ or other anti-PAP.

The following Examples are given to illustrate the present invention.

In these Examples, single letter and three letter amino acid abbreviations are used as follows:

| D | Asp | Aspartic Acid |
|---|-----|---------------|
| K | Lys | Lysine |
| Y | Tyr | Tyrosine |
| C | Cys | Cysteine |
| A | Ala | Alanine |
| P | Pro | Proline |
| F | Phe | Phenylalanine |
| S | Ser | Serine |
| G | Gly | Glycine |
| I | Ile | Isoleucine |

| R | Arg | Arginine |
| T | Thr | Threonine |

Synthesis of ASP4-LYS (D4K) Peptides

Peptides corresponding to the activation peptides found in human trypsinogens, Asp-Asp-Asp-Asp-Lys (D4K), and Ala-Pro-Phe-Asp-Asp-Asp-Asp-Lys (APFD4K), were synthesised with extra residues Tyr and Cys on their respective N-termini to provide sidechains that could be chemically cross-linked to protein carriers. Since the D4K sequence is degraded by aggressive acids, the base labile N-fluroeneylmethoxycarbonyl (Fmoc) group was used for reverible α-N-terminal protection [47]. The peptides YD4K and CAPFD4K were assembled on polystyrene solid phase supports with the acid-labile p-alkoxybenzyl alcohol C-terminal linker [48]. A modification of the procedure of Meienhofer et al. [49] was used for the synthesis, omitting the dioxane:$H_2O$ wash which was found to be unnecessary, and deprotecting with 20% piperidine in DMF rather than dichloromethane.

Our initial studies showed that if one protected aspartyl group was coupled to the immobilised C-terminal (N-t-Boc)Lys residue, the dipeptide Asp-Lys cyclised to a diketopiperazine on base-catalysed removal of the α-amino Fmoc group, and the moiety was released from the resin. The tetra-aspartyl sequence was therefore assembled using protected Asp-Asp dipeptides previously prepared, using hydroxybenzotriazole coupling to suppress racemisation during coupling to the resin-bound peptide. Completion of peptide bond formation after each addition was monitored with ninhydrin, or fluorescamine for Proline. Double couplings were required for each Asp-Asp dipeptide and for Fmoc(Trt-)Cys. After simultaneous cleavage from the resin and deprotection of t-butyl side chain protecting groups with 50% TFA in $CH_2Cl_2$ (containing also 5% ethyl methyl sulphide in the case of CAPFD4K), peptides were purified by successive gel filtration and ion-exchange chromotography to yield the required peptides in 62% (YD4K) and 35% (CAPFD4K) yields. The peptides were shown to be homogenous as single ninhydrin-positive spots on high voltage paper electrophoresis at pH 6.5 ($R_{Asp}YD_4K$ = 0.79, and $R_{Asp}CAPFD_4K$ = 0.76), and satisfactory amino acid analysis after acid hydrolysis. We have previously shown by $^{13}C$-NMR that trypsinogen activation peptides synthesised by this procedure are free of α-β transpeptidation [50].

Haptenisation of D4K Peptides

Two haptens were prepared by specific amino terminal coupling of synthetic trypsinogen activation peptides to protein carriers. YD4K was cross-linked to bovine serum albumin (BSA) by bis-diazotisation with the Tyr residue using benzidine dihydrochloride as described by Bassiri and Utiger (1972) [51]. Amino acid analysis of the purified adduct BSA-YD4K showed a substitution of 8 peptides per BSA molecule. The sulphydryl group of the peptide CAPFD4K was coupled to ε-amino groups of Lys on bovine thyroglobulin (TG) using the heterobifunctional linker m-moleimidobenzoyl-N-hydroxysuccinimide [52] to yield TG-CAPFD4K with a substitution of 40 molecules of peptide per thyroglobulin molecule.

Generation of Specific Anti-D4K Antisera

Emulsions of equal amounts of Freund's complete adjuvant (Miles Laboratories) with BSA-YD4K 2.9 mg/ml or TG-CAPFD4K 1.1 mg/ml were prepared by sonication on ice. NSW rabbits were immunised intradermally and intramuscularly with 2.0 ml of one or other emulsion and boosted using emulsions or corresponding hapten-peptide with Freund's incomplete adjuvant given each month. Sera were obtained before immunisation and 10 days after each challenge and tested for the presence of anti-D4K antibodies using a solid-phase immunoradiometric assay. BSA-YD4K and TG-CAPFD4K conjugates were immobilised in separate 96-well polyvinylchloride microtitre plates (Dynatech No 1-220-24) by incubation of 50 μl at 60 μg/ml protein in 50 mm Tris-HCl, 20 mM $CaCl_2$, 0.1% sodium azide (TCA-buffer) at 4° C. for 16 h. Plates were then washed at room temperature with TCA-containing 10% (v/v) heat-irradiated horse serum (TCA-HS, Tissue Culture Services, Berkshire, UK), and excess sites blocked by incubation with TCA-HS for 1 h. 50 μl aliquots of immune sera to be tested were then added to the wells in the presence or absence of D4K $10^{-5}M$ and incubated for 2 h at room temperature. Antisera from rabbits challenged with BSA-YD4K was tested on imobilised TG-CAPFD4K and vice-versa. Plates were then washed ×3 with TCA-HS and incubated for a further 16h with 50l 125I-goat antirabbit Ig (Miles AFA) 50,000 cpm per well in TCA-HS. Plates were washed, dried, and the wells counted in an LKB gamma counter. Titre of specific anti-D4K antibody was obtained from the difference in cpm bound in the presence or absence of competing D4K peptide $10^{-5}M$.

3 of 6 rabbits immunised with BSA-YD4K developed anti-D4K antibodies within 3 weeks. The titre in these animals increased over 2 to 3 months, then declined. In 2 of these animals the titre rose again with continued challenge to peak at 4 and again at 6 months. Three of the 4 rabbits immunised with TG-CAPFD4K responded with anti-D4K antibodies with peaks in the specific antibody titre at 2 and 3 and again at 6 months.

The presence of $Ca^{2+}$ ion was found to enhance the binding of antibodies in immune sera to activation peptides, the extent of enhancement being different in individual rabbits. The sera from one rabbit (1) exhibited total dependance on $Ca^{2+}$ binding to $^{125}I$-YD K being reduced to background level in the presence of chelating amounts of EDTA. In 3 rabbits (FIG. 1) binding increased in a concentration-dependant manner to a maximum observed at and above 1 mM $Ca^{2+}$ and thereafter fell up to 40 mM $Ca^{2+}$. Other divalent metal ions tested $Mg^{2+}$, $Zn^{2+}$, $Ba^{2+}$, $Hg^{2+}$ did not increase binding. The $Ca^{2+}$ dependency of subpopulations of anti-D4K antibodies was thought to be the result of the $Ca^{2+}$ chelating properties of the two available pairs of Asp-( carboxyls and the selective recognition of the peptide-$Ca^{2+}$ chelate, rather than D4K peptide alone, by rabbit host immunocytes following spontaneous $Ca^{2+}$ binding in vivo.

Affinity Purification of Anti-D4K Ig From Specific Antisera

Preparation of affinity adsorbant

Activated CH-Sepharose 4B (Pharmacia Fine Chemicals) was suspended in 1 mM HCl (100 ml), and washed with a further 900 ml of 1 mM HCl. Then Tyr-Asp-Asp- Asp-Asp-Lys (60 mg) in 25 ml of 0.1 M NaHCO$_3$ containing 0.5 M NaCl was added and the gel shaken for 1 h at 4° C. Excess ligand was washed away with 100 ml of 0.1 M NaHCO$_3$, and remaining active sites blocked by shaking the gel with 0.1 M Tris-HCl (pH 8) at 4° C. for 1 h. The gel was then washed with 50 ml 0.1 M sodium acetate (pH 4) containing 0.5 M NaCl. 50 ml 0.1 l Tris-HCl (pH 8), then these were washed twice more.

A small portion of the gel, hydrolysed in 6 M HCl at 110° C. for 20 h, and subjected to amino acid analysis, showed that the extent of substitution was 1.10 mmols/ml of gel.

Affinity chromatography on immobilised YD$_4$K

Two serum samples taken 6 weeks apart from rabbits, 1 and 2 (R$_1$, R$_2$) immunised with BSA-YD$_4$K, were pooled separately. Two similar samples from R17 and R18 immunised with TG-CAPFD$_4$K were pooled together. These pooled sera were subjected separately to affinity chromatography as follows: equal volumes of saturated solutions of ammonium sulphate were added to the sera, and the mixture left overnight at 4° C. The precipitated proteins were collected by centrifugation at 9,200 xgav at 4° C., and resuspended in the original volumes (see Table 1) of 50mM Tris-HCl (pH 7.4), 150 mM NaCl, 20 mM CaCl$_2$, and dialysed against two 2-liter changes of the same buffer. The dialysed protein was applied to a 1.5×10 cm column of the Sepharose-immobilised D$_4$K affinity matrix at a flow rate of 20 ml/h. Unbound protein was eluted with operational buffer until absorbance returned to zero. Then Ca$^{2+}$-dependent antibodies were displaced using 50 mM Tris (pH 7.4), 150 mM NaCl with 50mM EDTA followed by elution of Ca$^{2+}$-independent antibodies with 1 M propionic acid. Fractions were dialysed, assayed for activity by binding $^{125}$I-YD$_4$K (specific radioactivity 2.7×10$^8$ cpm/μg and antibody containing fractions pooled.

Figure 2:
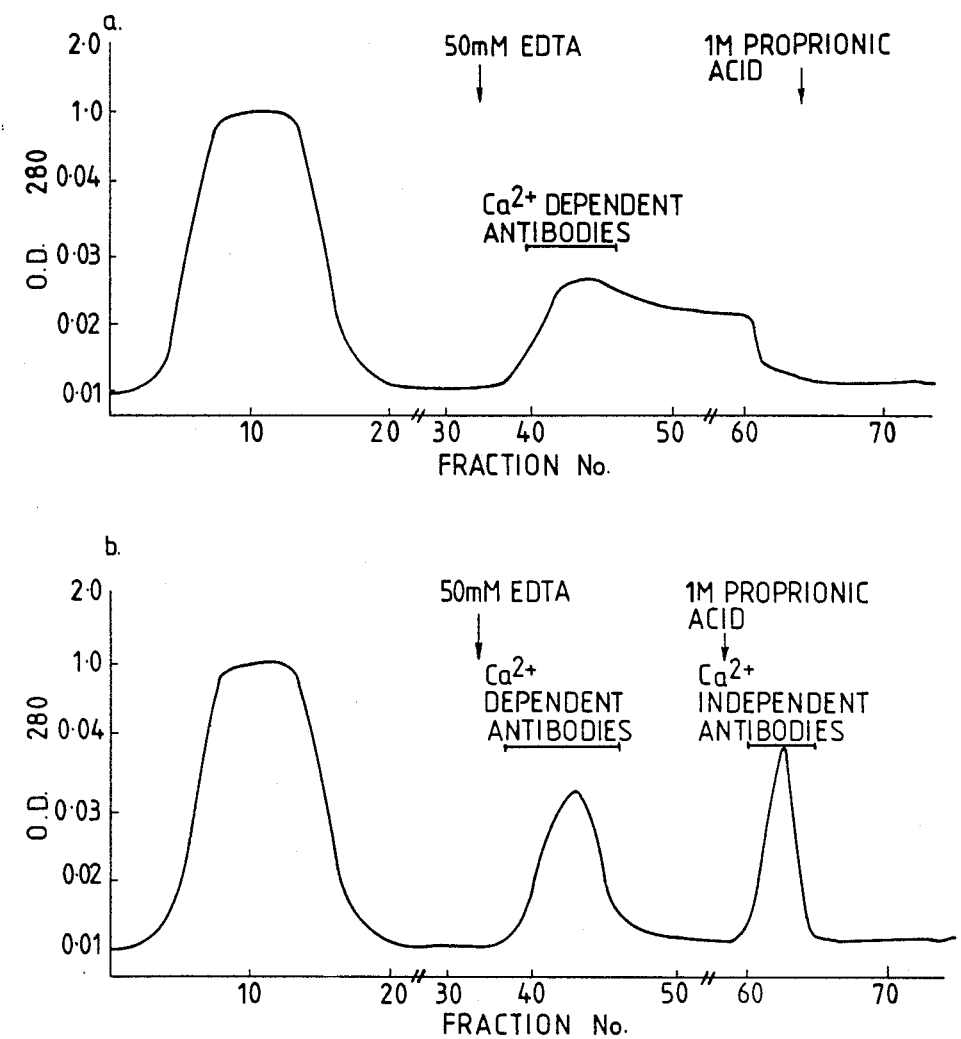
FIG. 2 shows elution profiles of anti-D$_4$K antisera after affinity chromatography on immobilized D$_4$K, showing the presence of $Ca^{2+}$-dependent and $Ca^{2+}$-independent antibodies.

The elution profile of immunoglobulins from rabbit 1 showed that a wide peak of antibodies was obtained by elution with EDTA, but no protein or antibody eluted in 1 M propionic acid (FIG. 2a), confirming that anti-D$_4$K antibodies present in this serum were Ca$^{2+}$-dependent. Table 1 shows that antisera from Rabbit 2 which had also been immunised with BSA-YD$_4$K contained Ca$^{2+}$-dependent and Ca$^{2+}$-independent anti-D$_4$K antibodies. This suggests the presence of 2 epitopes on the D$_4$K molecule and that the recognition of one or both depended on the individual animal. The elution profile of pooled sera from rabbits 17 and 18 immunised with TG-CAPFD$_4$K (FIG. 2b) demonstrates both Ca$^{2+}$-dependent antibodies displaced with EDTA and Ca$^{2+}$-independent antibodies displaced using 1 M propionic acid.

TABLE 1

AFFINITY PURIFICATION ON YD$_4$K LINKED TO SEPHAROSE OF CALCIUM-DEPENDENT AND CALCIUM-INDEPENDENT ANTIBODIES

| | Vol (ml) | Total Protein (mg) | Total Activity | Specific Activity | Yield | Purification |
|---|---|---|---|---|---|---|
| Rabbit 1 - Immunised with BSA-YD$_4$K: | | | | | | |
| Pooled serum | 5 | 500 | 175$^a$ | 0.35 | 100 | 1 |
| EDTA-peak | 5 | 0.63 | 105$^a$ | 66 | 60 | 180 |
| Proprionic acid peak | 8 | 0 | 0$^a$ | 0 | 0 | — |
| Rabbit 2 - Immunised with BSA-YD$_4$K: | | | | | | |
| Pooled serum | 16 | 1092 | 286$^b$ | 0.26 | 100 | 1 |
| EDTA-peak | 11 | 3.3 | 48$^b$ | 14.3 | 16.7 | 55 |
| Proprionic acid peak | 37 | 9.0 | 152$^b$ | 17.0 | 53.2 | 65 |
| Rabbits 17/18 - Immunised with TG-CAPFD$_4$K: | | | | | | |
| Pooled serum | 21 | 1848 | 709$^b$ | 0.38 | 100 | 1 |
| EDTA-peak | 52 | 9.5 | 90$^b$ | 9.47 | 12.7 | 74 |
| Proprionic acid peak | 44 | 10.5 | 613$^b$ | 58.3 | 86.4 | 174 |

$^a$% binding to $^{125}$I-YD$_4$K at 1:1,000 dilution X volume (ml)
$^b$difference in cpm in presence of 10$^{-5}$ M D$_4$K and absence of D$_4$K binding to immobilised peptide at 1:100 dilution; detection by $^{125}$I-goat anti-rabbit X volume (ml)

Specificity of Antibodies For C-Terminal D$_4$K Peptides

Figure 3:
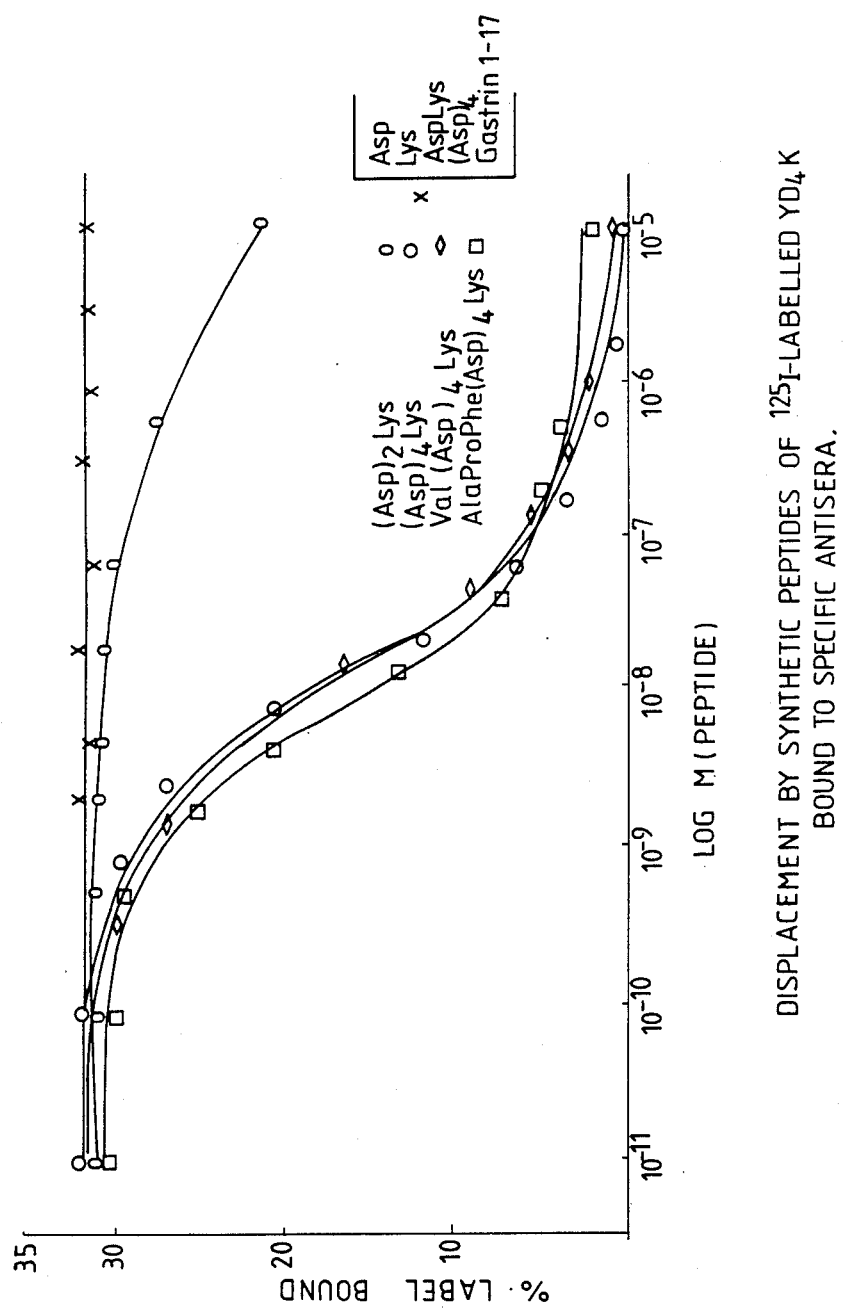
FIG. 3 demonstrates displacement by synthetic peptides of $^{125}$I-labeled YD$_4$K bound to specific antisera.

The relative affinities of affinity-purified Ca$^{2+}$-dependent antibodies present in sera from Rabbit 1 for various peptides was examined by determining competition of binding to $^{125}$I-YD$_4$K, measured by precipitation with a second antibody, donkey anti-rabbit. Synthetic peptides D$_4$K, VD$_4$K and APFD$_4$K, displaced binding at similar concentrations (FIG. 3) with IC$_{50}$ values all in the region of 10$^{-8}$M. In contrast Asp, Lys, Asp-Lys, Asp-Glu, poly-Asp, and human gastrin (residues 1 to 17 containing a pentaGlu sequence) did not displace binding to $^{125}$I-YD$_4$K at concentrations as high as 10$^{-4}$ M (FIG. 3). Some binding to Asp$_2$Lys was seen. Affinity purified Ca$^{2+}$-dependent and Ca$^{2+}$-independent antibodies from other rabbits showed a very similar specific affinity and specificity for tetra-L-aspartyl-L-lysine sequences.

Figure 4:
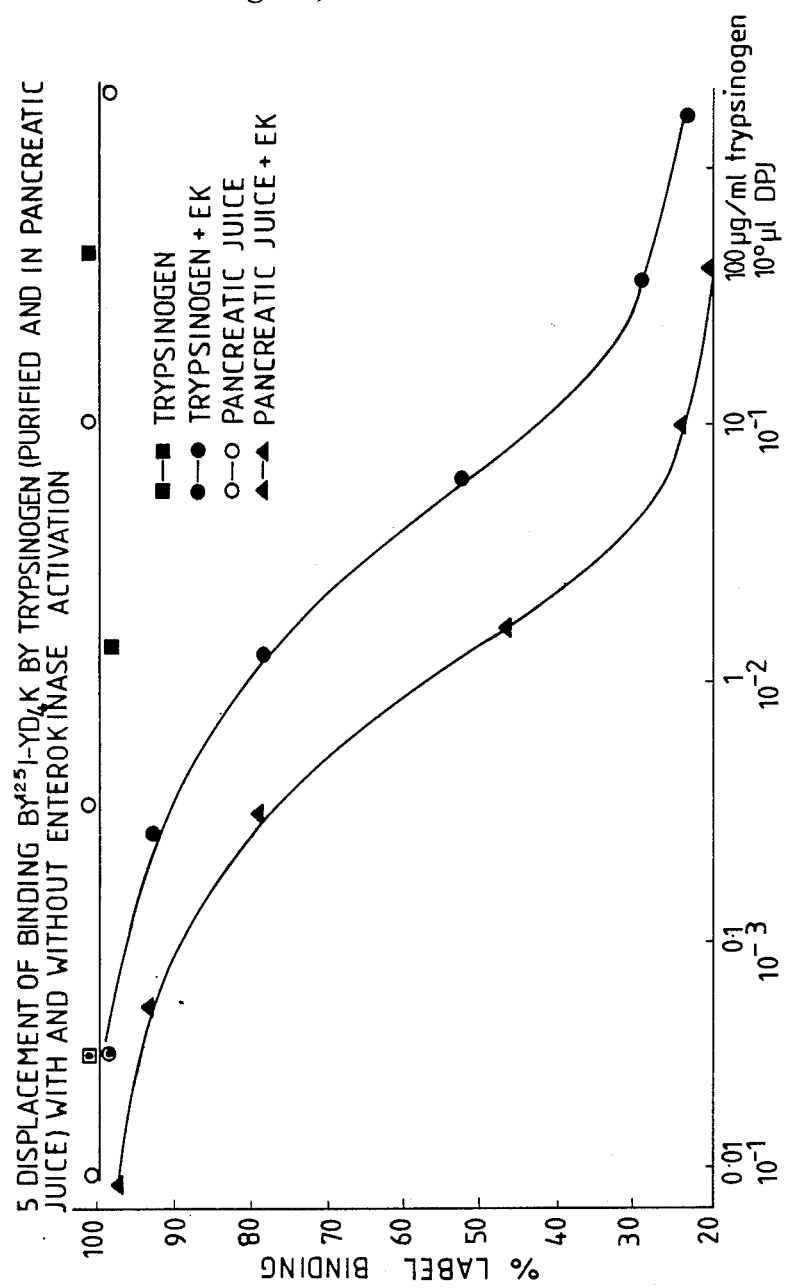
FIG. 4 shows displacement of binding by $^{125}$I-YD$_4$K by trypsinogen (purified and in pancreatic juice) with and without enterokinase activation.

Of great importance to the general principle of the PAP assay of which this is an example, and for the application of these specific anti-D$_4$K antibodies to the diagnosis of pancreatic disease was the finding that anti-D$_4$K antibodies were C-terminally directed on the peptide, and were not displaced by trypsinogen (where the peptide is C-terminally bound to the protein) in concentrations of the zymogen of up to 100 μg/ml. Upon incubation of trypsinogen with enteropeptidase, however, released D$_4$K-containing activation peptides actively displaced the binding of synthetic $^{125}$I-YD$_4$K giving 50% displacement after activation of a 2 μg/ml solution of trypsinogen (FIG. 4). Trypsinogen in native dog pancreatic juice was also activated by enteropeptidase (FIG. 4) releasing immunoreactive D$_4$K peptides, giving 50% displacement in competitive solution-phase immunoassay after activation of 10$^{-8}$L pancreatic juice. The novel D$_4$K-specific antibodies described here therefore also provide a new sensitive assay for enteropeptidase and trypsinogen applicable to fluids with endogenous trypsin inhibitors.

The singular specificity for D$_4$K peptides of the novel anti-D$_4$K antibodies we produced, was further demonstrated by examining skin secretions of the amphibian Xenopus laevis. Tetra-aspartyl-lysyl peptides as internal sequences in larger proteins, had been predicted to occur in the skin of this species by finding the corresponding nucleic acid sequence in cDNA clones derived from cutaneous mRNA [53]. Skin secretions from this amphibian are known to contain a variety of peptides with counterparts in the mammalian nervous system including CCK, gastrin, enkephalin, TRH, and somatostatin. We obtained a crude peptide extract derived from the skin of this species and subjected it to reverse-phase HPLC on a C8 column. The elution profile demonstrating multiple peptides is shown in FIG. 5. Only two peaks immunoreactive for $D_4K$ peptides were, however, identified and these co-chromatographed with the migration positions identified in this system for synthetic $D_4K$ and $APFD_4K$. Free $D_4K$ C-termini were thought to have been generated in the crude peptide mixture by processing of precursors, although the titre of available $D_4K$ C-termini was increased by tryptic hydrolysis of the peptide extract indicating the presence of some unprocessed precursor. $D_4K$ sequences in frog skin are thought to arise as a result of distant evolutionary relationships to mammalian trypsinogens. The specific recognition of $D_4K$ peptide in the crude mixture obtained from this amphibian, further demonstrates the specificity of the affinity-purified anti-$D_4K$ antibody.

Immunoassay of $D_4K$ Peptides

Solution phase competitive immunoradiometric assay

100 μl of a 1:250 dilution of anti-$D_4K$ antiserum or a dilution of affinity-purified anti-$D_4K$ antibodies in 50 mM Tris-HCl, 20 mM $CaCl_2$, 0.1% (w/v) BSA, pH 7.4 (RIA buffer) were added to 100 μl of $^{125}I$-$YD_4K$, (10,000 cpm) in RIA buffer containing 0.2% (v/v) normal rabbit serum in polystyrene tubes. Then 100 μl of solutions containing various concentrations of standard peptides or unknown plasma samples diluted in RIA-buffer were added, followed by 50 μl of donkey anti-rabbit Ig serum (Wellcome Biotechnology) diluted 1:10 with RIA-buffer with 0.2% normal rabbit serum. The mixtures were incubated 18 h at 4° C., then the tubes were centrifuged at 3,000 rpm for 45 min at 4° C., and the supernatants aspirated. The radioactivity in the precipitates was determined in an LKB rack-gamma counter.

Solid-phase competitive immunoradiometric assay

Figure 6:
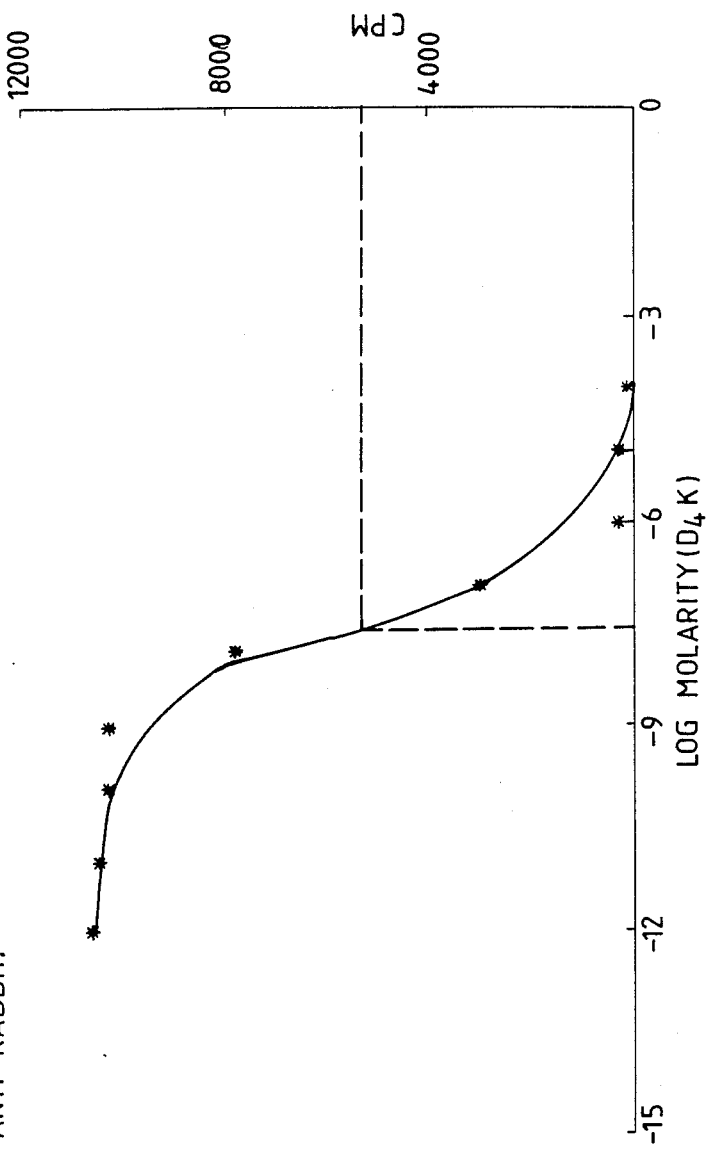
FIG. 6 shows the results of radiometric assay-type 1 wherein wells were coated with 60 ug/ml solution of YD$_4$K-BSA and tested with $Ca^{2+}$-independent antibody at a working dilution of 1:50. Displacement with D$_4$K and detection with $^{125}$I-goat anti-rabbit antibody is shown.

In order to improve the ease and sensitivity of immunoassay over that associated with competitive precipitation radioimmunoassay, two types of assay were developed using solid-phase techniques. In the first type, wells of PVC microtitre plates were first coated with BSA-$YD_4K$ at 60 [g/ml protein concentration. Then standard concentrations of synthetic activation peptides were preincubated with affinity-purified anti-$D_4K$ antibodies and applied to the wells. Antibody adhering to the immobilised peptide hapten was then determined with $^{125}I$-labelled goat anti-rabbit antibody. A typical standard curve is shown in FIG. 6, using $Ca^{2+}$-independent antibody. A steep dependence on the concentration of competing peptide was apparent over the range $10^{-6}$ M to $10^{-9}$ M with $IC_{50}$ value of $5 \times 10^{-7}$.

Figure 7:
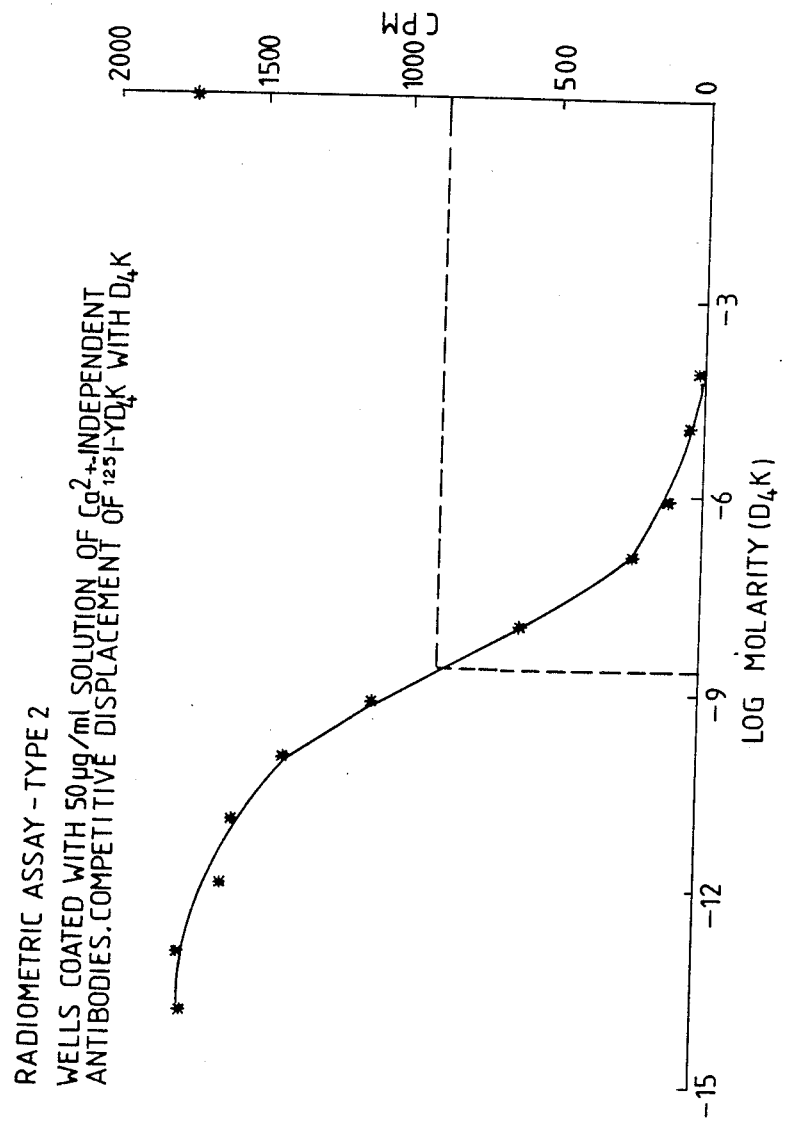
FIG. 7 depicts the results of radiometric assay-type 2 wherein wells were coated with 50 ug/ml solution of $Ca^{2+}$-independent antibodies. Competitive displacement of $^{125}$I-YD$_4$K with D$_4$K is shown.

A second type of radiometric assay was developed using immobilised affinity-purified anti-$D_4K$ antibody. Wells of microtitre plates were coated with 50 μl of $Ca^{2+}$ independent antibodies (50 μg/ml) at 4° C. overnight, in 50 mM Tris-HCl (pH 7.4) with 0.1% (w/v) sodium azide. Plates were then washed three times with 50 mM Tris-HCl (pH 7.4) containing 10% horse-serum (T-HS buffer), and incubated with T-HS buffer for 1 h at room temperature to block remaining sites. Solutions (60 μl) were prepared containing $^{125}I$-$YD_4K$, (100,000 cpm) and various concentrations of $D_4K$ ($10^{-4}M - 10^{-13}M$), in T-HS buffer. 50 μl aliquots were transferred to the antibody-coated wells, then incubated at room temperature for 5 h. Plates were washed with T-HS buffer three times, and left to dry at room temperature. The wells were cut out and radioactivity determined as described. The results (FIG. 7) showed a wider dependence on cpm bound between $10^{-6}M$ and $10^{-12}M$ of competing peptide, and an $IC_{50}$ value of about $10^{-9}M$, representing a 10-fold increase in sensitivity.

Solid-phase enzyme-linked immunoassay

Benzidine dihydrochloride (10.2 mg) in 0.2 M HCl (2 ml) was diazotised by addition of sodium nitrite (7.8 mg) in water (0.2 ml) for 1 h at 4° C., then buffered to pH 9 with 3.2 ml of 0.25 M sodium borate/0.2 M NaCl. Then $YD_4K$ (4.9 mg) was coupled to horse-radish peroxidase (Sigma; 49.2 mg) in 10.8 ml 0.16 M sodium borate/0.14 M NaCl (pH 9) by addition of the benzidine reagent at +4° C., and incubating for 2 h. Excess reagents and peptide were removed by extensive dialysis against 0.15 M NaCl, water, then 0.15 M NaCl to yield a solution of conjugate of 3.2 mg/ml.

ELISA assay was performed as described above for the second type of radiometric assay using plates coated with $Ca^{2+}$ independent antibody (25 μg/ml) in 50 mM Tris (pH 7.4), 0.1% sodium azide. Plates were washed three times with 50 mM Tris (pH 7.4), 10% (v/v) horse serum, 0.5% Tween 20, blocked with 50 mM Tris (pH 7.4), 10% (v/v) horse serum for 30 min, then incubated with a mixture of 1:10,000 peroxidase-$D_4K$ peptide conjugate and unknown samples or standard amounts of peptide in 50 mM Tris (pH 7.4), 0.05% Tween 20. After h at 20° C., the plates were washed three times and developed by incubation with 3,3',5,5'- tetramethylenebenzidine (0.01% [w/v] in 0.1 M sodium acetate/citric acid [pH 6.6]) for 1 h at 20° C. The reaction was stopped by addition of 50 ml 2 M $H_2SO_4$, and colour estimated at 450 nm. The resulting displacement curve exhibited similar sensitivity to the radiometric assay shown in FIG. 7.

Assay of the Stability and Distribution of $D_4K$ Peptides In Vivo

The $D_4K$ peptide was found to be stable in human serum, and activated pancreatic juice. Immunoreactive $D_4K$ was unaltered by incubation with undenatured human serum at 37° C. for 6 h and 4° C. for 48 h. Sephadex G-100 chromatography of $YD_4K$ after incubation in human serum showed that the immunoreactive $D_4K$ peptide co-chromatographed with free peptide in buffer and did not complex with a serum component.

The stability of $APFD_4K$ and $D_4K$ were examined by incubation with activated pancreatic juice, and the chemical identity of the product examined by high-voltage paper electrophoresis at pH 6.5. The results showed that $APFD_4K$ was rapidly converted to free Ala, Pro and Phe and $D_4K$, but that the $D_4K$ sequence itself was stable for 24 h at 37° C. In three separate experiments, duplicate 65 to 75 mg portions of fresh dog pancreas were placed in modified Bank's medium and incubated in the presence or absence of 100 units enterokinase (Sigma Chem. Co. E0885) at 37° for 4 hours and 22° C. for a further 20 hours. Duplicate 100 μl samples of culture medium supernatant were taken at intervals, diluted 2:1 with RIA buffer, boiled for 10 mins and centrifuged. Supernatants were then stored at −20° C. prior to assay for $D_4K$ peptides.

Figure 8:
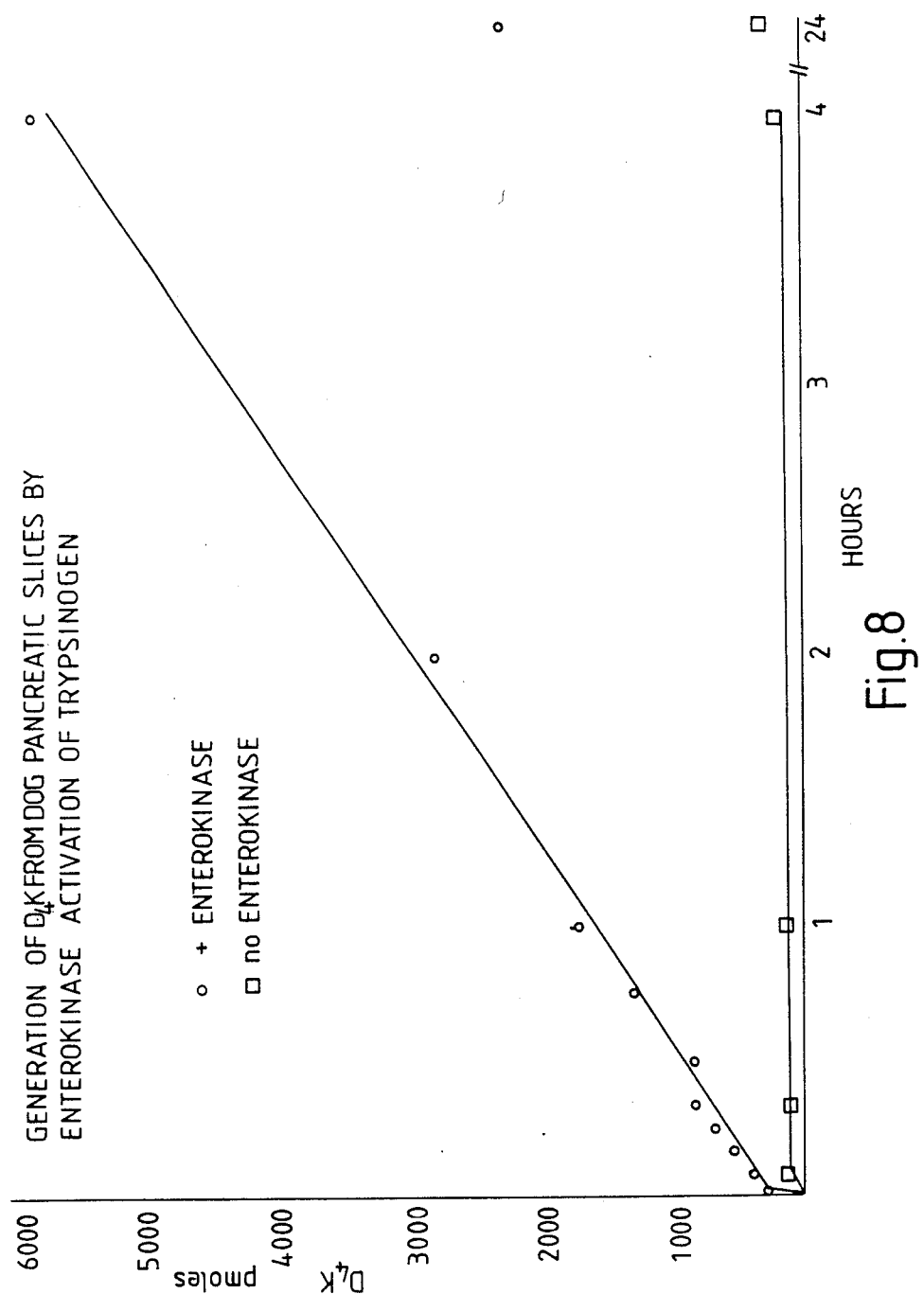
FIG. 8 demonstrates the generation of D$_4$K from dog pancreatic slices by enterokinase activation of trypsinogen.

In each of the three experiments incubation with enterokinase was associated with degradation of pancreatic tissue and rapid release of immunoreactive $D_4K$ peptides. These changes were not seen in short term cultures without enterokinase (FIG. 8). $D_4K$ immunoreactive peptides in the culture medium persisted at high levels after 24 hours incubation demonstrating their resistance to combined pancreatic proteolysis.

Figure 9:
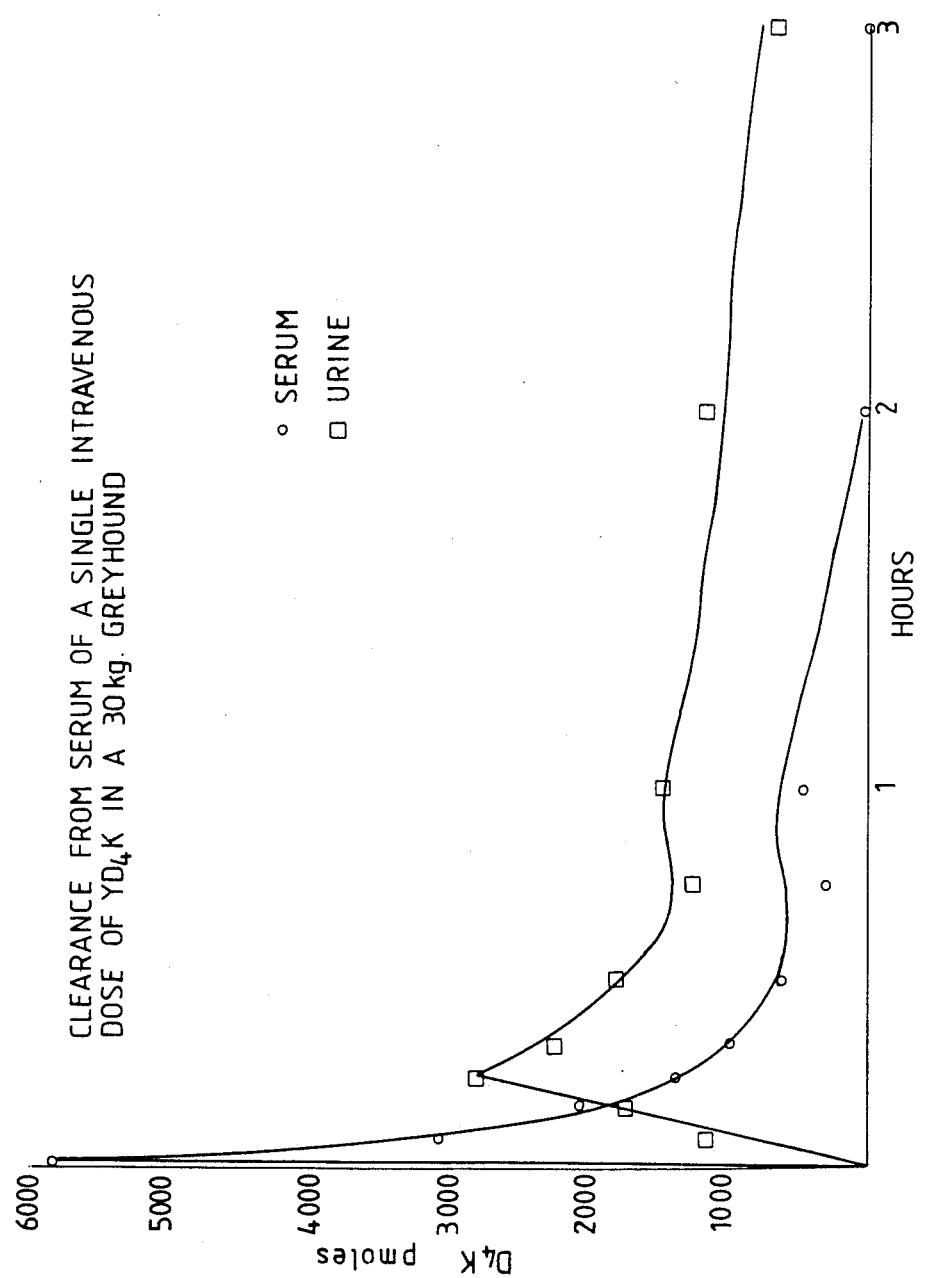
FIG. 9 shows the clearance from serum of a single intravenous dose of YD$_4$K in a 30 kg greyhound.

To determine the fate of circulating peptide, $D_4K$ (0.28 ml, 1 mg/ml) was injected into the left femoral vein of rats under phenobarbital anaesthesia. Blood samples (0.5 ml) were collected every 15 min for 2 h, and subjected to immunoassay. The results showed that administered immunoreactive $D_4K$ disappeared from serum in vivo with half-life of about 15 min. In a second series of such experiments $YD_4K$ 100 μg/kg in 1 ml PBS was injected intravenously in each of 3 healthy fasted greyhound dogs. Samples of blood and urine were obtained at intervals over 4 hours and stored at −20° C. prior to assay. The mean half-life of $D_4K$ peptide in blood was 8.3 mins in dogs but in each case $D_4K$ was detectable in serum for 2 hours. $D_4K$ appeared in urine within 5 minutes of intravenous administration and persisted longer, for 3 to 4 hours.(FIG. 9)

A limited study was carried out to determine the tissue distribution of immunoreactive $D_4K$ peptides. Extracts of rat brain, pancreas, duodenum and pituitary were prepared by homogenisation and sonication in 24 mM HCl containing pepstatin 0.1 mg/ml, chymostatin 0.1 mg/ml, elastinal 0.1 mg/ml, and Trasylol 2000 KN/ml. Extracts were adjusted to pH 5.6, diluted with 0.1 M succinate buffer pH 5.6, and digested with enteropeptidase for 1 h at 37° C. $6 \times 10^{-7}$ moles $D_4K$/mg protein and $1.5 \times 10^{-7}$ moles $D_4K$/mg protein were found after enteropeptidase digestion in extracts of rat pancreas and duodenum respectively. No D peptide was detected in extracts of rat brain or pituitary, and none was found after assay of extracts of guinea-pig brain similarly prepared. Canine pancreatic juice obtained by cannulation of the main pancreatic duct followed by CCK stimulation, showed no immunoreactive $D_4K$ peptide before enteropeptidase activation and $5.7 \times 10^{-4}$ moles $D_4K$/ml after activation. No $D_4K$ immunoreactivity was identified in fasting or postprandial serum or urine in multiple samples from 3 dogs and 6 normal human subjects. No $D_4K$ immunoreactivity was found in serum samples of patients with perforated duodenal ulcer, mesenteric infarction, appendicitis, aortic aneurysm, Crohn's disease or gastrointestinal haemorrhage. No $D_4K$ was found in human sera in association with Altzheimer's disease, rheumatoid arthritis or any other non pancreatic disease state tested.

Assay of $D_4$ Peptide in Experimental and Human Pancreatitis

Acute necrotising pancreatitis was induced experimentally in 22 anaesthetised rats by the controlled intrapancreatic duct microinfusion over 30 minutes of 75 μl buffer containing 10–20 mmol/l glycodeoxycholate alone or with 50 ng highly-purified human enteropeptidase [54]. The rats subsequently received continuous intravenous analgesia together with pancreatic stimulation using CCK-33 10 IDU/kg/h. Blood was taken before the intraduct infusion and 3 hours afterwards, and assayed for free $D_4K$ peptide. Histological examination of the pancreas showed severe acute pancreatitis in every case. Circulating immunoreactive $D_4K$ peptide rose with the development of the disease in each of the 22 animals from an apparent mean basal level of 5 pmole/ml to a mean of 84 pmole/ml after 3 hours. By contrast no free $D_4K$ peptides were identified in pancreas homogenates from 6 mice with acute oedematous pancreatitis induced by CCK-8 hyperstimulation [55].

Preliminary clinical studies were carried out to determine whether $D_4K$ peptide could be identified in serum or urine from severe acute pancreatitis patients as predicted. Random serum and in some cases urine samples were accumulated from 22 patients with pancreatitis. Not all of these samples were taken during the early hours of the disease. On the basis of Ranson's criteria [56] 14 patients were classified as having the milder oedematous form of pancreatitis and 8 patients were assessed as having the severe necrotising form of the disease. No immunoreactive $D_4K$ peptide was found in samples from any of the patients with the oedematous disease, despite substantial elevation of the serum amylase in all of them, whereas $D_4K$ was identified in samples of serum and/or urine from 6 of the 8 judged to have severe pancreatitis.(Table 2)

TABLE 2

| Initial | Age | Aetiology | | | Pancreatitis | | $D_4K$ | |
|---|---|---|---|---|---|---|---|---|
| | | GS | Etoh | Other | Mild | Severe | Urine | Serum |
| M.B. | 76 | + | | | | + | + | |
| H.B. | 50 | | | + | + | | | |
| J.B. | 84 | + | | | + | | | |
| D.D. | 53 | + | | | | + | | + |
| D.G. | 70 | + | | | + | | | |
| R.G. | 66 | + | | | | + | | |
| W.G. | 56 | | | + | | + | | + |
| A.J. | 38 | | + | | + | | | |
| D.K. | 84 | | | + | + | | | |
| J.K. | 33 | | + | | + | | | |
| P.L. | 67 | | | + | | + | | |
| G.M. | 41 | | | + | + | | | |
| T.N. | 63 | | | + | + | | | |
| V.N. | 30 | | + | | + | | | |
| I.N. | 53 | + | | | + | | | |
| T.P. | 43 | | + | | + | | | |
| J.P. | 68 | | | + | + | | | |
| M.R. | 36 | | + | | + | | | |
| A.R. | 81 | + | | | + | | | |
| C.R. | 54 | + | | | | + | + | + |
| O.S. | 48 | | | + | | + | | + |
| J.S. | 45 | | | + | | + | + | + |

TAP Assay of random samples collected at St. George's January 1985-March 1987. Stored at −20° C.

Figure 10:
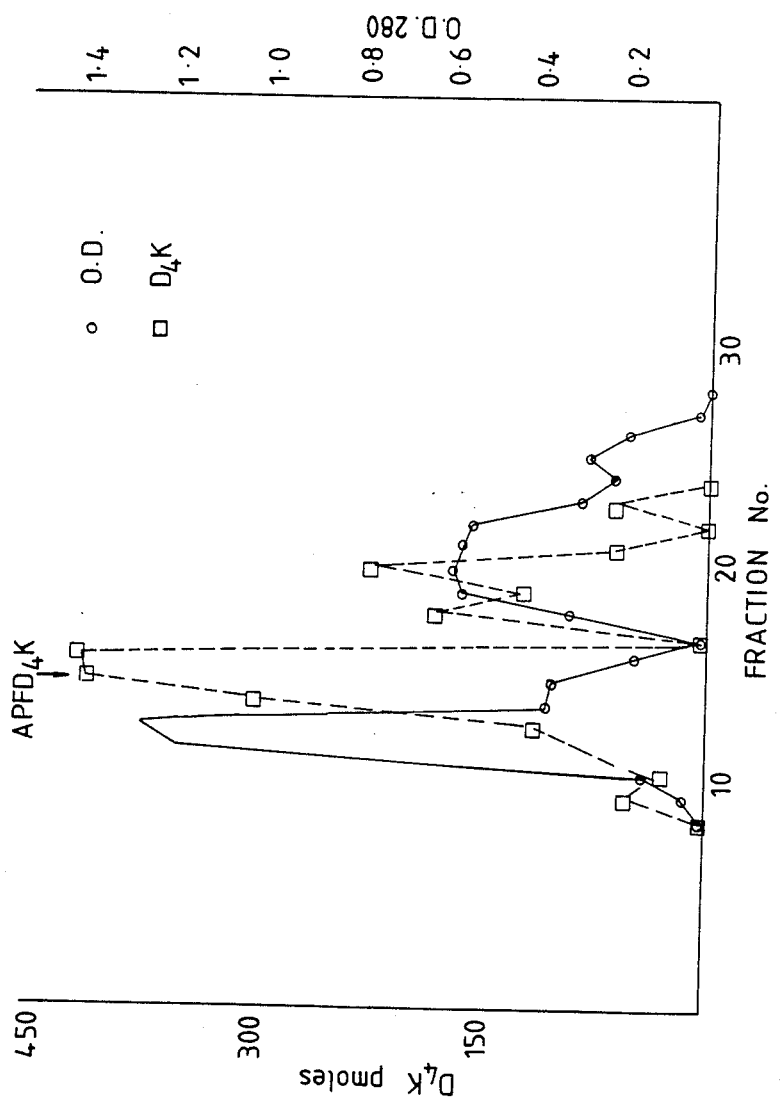
FIG. 10 depicts the elution profile on Sepharose G15 and the concentration of D$_4$K in samples of JS sera.

Chromatography of samples of JS sera on Sepharose G15 showed that the immunoreactivity comigrated with standard $APFD_4K$ (FIG. 10). In addition, serum was obtained from one patient (PD) who presented with abdominal pain and an exacerbation of chronic pancreatitis for which he had previously had a 75% distal pancreatic resection. $D_4K$ peptide was detected in this sample at the level of $10^{-8}$ M.

Figure 11:
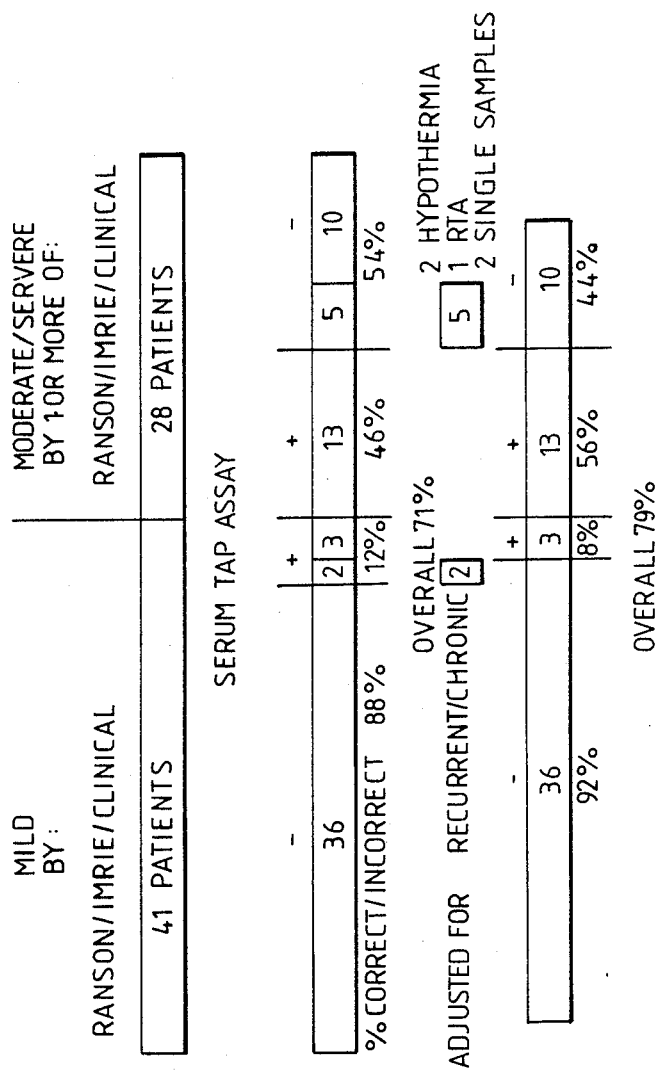
FIG. 11 shows the results of a TAP assay performed on pancreatic sera.

In a second clinical study assay for $D_4K$ peptides was carried out on sera accumulated during routine daily sampling from 69 patients admitted to the Glasgow Royal Infirmary, Scotland, and other hospitals in the Glasgow area (FIG. 11). Sera were stored frozen at −20° C. and had to be thawed, aliquoted, and refrozen prior to rethawing and assay. A total of 279 stored sera were available representing serum samples taken from the 69 patients for up to 5 days, but in a few cases only a single sample was available. Assay for D$_4$K peptides was performed blind without knowledge of the severity or clinical course of the pancreatitis. 36 of 39 patients (92%) assessed as having oedematous pancreatitis were D$_4$K negative and 13 of 23 more severe cases (56%) were D$_4$K positive. The overall accuracy of the D$_4$K assay performed retrospectively on routine frozen-thawed-frozen-thawed serum-only samples in this series was 79%. Apparent false positives (3) probably reflect the known inadequacy of the clinical assessment method. Apparent false negatives (10) are likely to reflect this, together with errors introduced by the dissociation of routine once a day serum sampling from changing clinical status, and the absence of the additional information contributed by a urinary assay.

3 patients admitted to St. George's Hospital, London, SW17, England, with acute pancreatitis and hyperamylasaemia were studied using the D$_4$K assay as intended, to monitor the severity and progress of the disease. To do this, simultaneous blood and (where available) urine samples were taken immediately on admission and at 4 to 6 hourly intervals for the first 48 hours and thereafter 8 hourly. Samples were stored frozen at $-20°$ C. prior to D$_4$K assay. One patient TP (FIG. 12) with moderate/severe pancreatitis but who later developed a pseudocyst, had an initial urinary D$_4$K level of 250 pmol ml$^{-1}$ 24 hours after admission but no D$_4$K detectable in serum at this time. This reflects the look-back capability of the urine assay and the prolonged urinary excretion of D$_4$K peptide after intravenous administration identified experimentally in dogs. On the fourth day of hospitalisation, D$_4$K peptides appeared transiently in serum and later rose in urine. These changes were matched by a distinct clinical exacerbation supporting the role of the D$_4$K and other PAP assays as a precise disease-course monitor.

In a second patient CM in this series with moderate pancreatitis but with respiratory insufficiency, serum D$_4$K was 38 pmol ml$^{-1}$ and urinary D$_4$K 100 pmol ml$^{-1}$ on admission. Both fell to zero within a few hours and thereafter remained negative, but a 2 cm pseudocyst and small lesser sac fluid collection was subsequently identified. This further supports the ability of D$_4$K assay to predict even small areas of pancreatic necrosis. The third patient in this group, CTM, admitted with abdominal pain and a serum amylase >7000 units, remained serum and urine D$_4$K negative over 5 days despite his initial signs(FIG. 12). He had gall stones with oedematous pancreatitis which subsequently resolved over 5 days. This again supports the role of a negative D$_4$K assay as an accurate severity indicator in the acute disease. These results also suggest that the significant number of false negative D$_4$K assays in the Glasgow serum-only study would not have occurred with frequent blood and urine sampling and the assay applied clinically as intended.

Additional serum samples from two patients with chronic recurrent pancreatitis in exacerbation showed D$_4$K peptides and serum amylase levels within normal limits; this would support the diagnostic capability of the D$_4$K assay in the chronic disease. Taken together the clinical and experimental findings with the D$_4$K assay provide strong support for the proposed role of the invention in the diagnosis, severity prediction, and disease-course-monitoring of pancreatitis. The findings also support the principle embodied in the invention for the specific assay of body fluids for free PAP molecules using C-terminally directed antibody in pancreatic diseases.

Other Pap Assays of the Invention

Activation peptides of other pancreatic zymogens which are suitable for specific assay using C-terminally directed antibodies for the free species, in accordance with the present invention, include those of prophospholipase A$_2$, procolipase, proelastase 1 and proelastase 2, prekallekreins and of procarboxypeptidases A & B. Examples of these are peptides containing the carboxy terminal sequence Asp-Ser-Gly-Ile-Ser-Pro-Arg of prophospholipase A$_2$[41], peptides containing carboxy terminal Ala-Pro-Gly-Pro-Arg of procolipase [42], and peptides containing carboxy terminal Gly-Asp-Pro-Thr-Tyr-Pro-Pro-Tyr-Val-Thr-Arg of proelastase 2 [43] or peptides representing the sequence of the activation peptides of proelastase 1 or prekallekreins. Portions of these sequences representing proteolytic degradation oligopeptides of 5 or more residues such as Pro-Pro-Tyr-Val-Thr-Arg from proelastase 2 may also be used. The much larger activation peptides of procarboxypeptidases A & B may also contain oligopeptide sequences suitable as targets. The use of C-terminally directed antibody will ensure that zymogen forms normally present in human plasma and urine [57] will not be recognised in the assay as in the segregation of D$_4$K containing free peptides from trypsinogens, already given as a detailed example.

Of additional interest and importance is the activation peptide of prophospholipase A$_2$ (PLAP). Prophospholipases A$_2$ are abundant in many cell types including macrophages [58] pulmonary alveolar macrophages [59], aggregated platelets, and polymorphnuclear leucocytes [61] as well as being generally present in lysosomes. Active phospholipase A$_2$ is released from these in several inflammatory conditions [62] including endotoxin shock [63], respiratory distress syndrome, acute abdominal conditions and in response to mycobacteria [61], peptides [60] and Ca$^{2+}$ [39]. If the prophospholipase A$_2$ from these sources is the same gene product as pancreatic prophospholipase A$_2$ and has an activation peptide of the same sequence Asp-Ser-Gly-Ile-Ser-Pro-Arg, PLAP assay as defined in this invention, will also be a useful test applicable to the recognition and severity prediction of these disorders. If the non pancreatic prophospholipase A$_2$ activation peptide has a sequence different from pancreatic prophospholipase A$_2$, then the PLAP assay will be pancreatic disease specific.

Synthesis of prophospholipase A$_2$ activation peptide (PLAP) and procolipase activation peptide (CLAP)

Further examples of the invention involve the synthesis by solid-phase methods, of peptides relevant to the development of immunoassays C-terminally specific for PLAP and CLAP. These peptides are Asp-Ser-Gly-Ile-Ser-Pro-Arg, Cys-Tyr-Asp-Ser-Gly-Ile-Ser-Pro-Arg, Ala-Pro-Gly-Pro-Arg and Cys-Tyr-Ala-Pro-Gly-Pro-Arg. Syntheses were performed on p-alkoxybenzyl-alcohol-derivatised polystyrene (0.67 m equivs/g from Bachem Feinchemikalien AG, Switzerland) using temporatory base-labile Fmoc/α-amino group protection and the general methods described by Cliffe et al [50] with the following modifications. The C-terminal residue was coupled as its protected derivative Fmoc (Mtr)Arg by a mixed anhydride method. Two equivalents of protected Arg were incubated with resin having one equivalent of alkoxybenzyl group, together with 2 equivalents of 2, 6-dichlorobenzoyl chloride and 3 of redistilled pyridine in dimethylformamide for 16 h. All subsequent Fmoc amino acids were coupled in a 2-fold excess as 1-hydroxybenzotriazole esters. The following derivatives were employed: Fmoc-Pro, Fmoc-(OtBu)Ser, Fmoc-Ile, Fmoc-Gly, Fmoc-(OtBu)Asp, Fmoc-(OtBu)Tyr and Fmoc-(SAcM)Cys. At the end of the synthesis, the N-terminal Fmoc group was cleaved by treatment with 20% (v/v) piperidine for 10 min and the peptide cleaved and partly deprotected by treatment with 50% (v/v) trifluoroacetic acid, 5% thioanisole, 45% (v/v) dichloromethane. This was evaporated washed four times with ether and lyophilised. Portions (250 mg) of those peptides containing protected (SAcM) cysteinyl groups were extracted into minimal volumes of water and adjusted to pH4 with $NH_4OH$. Then mercuric acetate (200 mg) was added and the pH readjusted to 4. After 1 hr, the peptide was diluted to 50 ml and $H_2S$ passed through the solution for 15 mins, followed by $N_2$ for 10 min. The black precipitate (HgS) was separated by centrifugation and the peptide recovered by lyophilisation.

Peptides were purified by gel chromatography on Sephadex G-15 in 0.1 M acetic acid and characterised by reverse phase HPLC and amino acid analysis. On Brownlee C-8 Aquapore RP-300 in 0.05% trifluoroacetic acid and acetonitrile from 5% to 25% (v/v) over 22 min at 1.0 ml/min peptides gave single peaks at 9.14 min for CYAPGPR, 5.49 min for APGPR. On µBondapak $C_{18}$ in 0.05% trifluoroacetic acid running and acetonitrile gradient 5% to 50% over 30 mins 1.5 ml/min CYDSGISPR eluted at 11.7 min and DSGISPR at 7.8 min. Amino acid analysis confirmed the correct composition of these peptides.

Peptides with Cys-Tyr amino terminal extensions are used for haptenisation or the attachment of revealing agent or solid phase, and native peptides for use on solid phase or as competing ligands as described in the $D_4K$ example of the invention. Specific C-terminal antibodies either polyclonal or monoclonal are purified by affinity chromatography on the corresponding immobilised peptide and used in the performance of solid or solution phase assays as detailed in the $D_4K$ example. Peptides with revealing agents or immobilised on solid phase as well as specific antipeptide antibodies with or without revealing agent, and free or attached to solid phase, and the use of such reagents in the performance of PAP assays in the diagnosis and severity monitoring of disease form further aspects of the invention.

BIBLIOGRAPHY

1. Corfield A .P. et al (1985). Gut 26: 724–729.
2. Hermon-Taylor J and Heywood G. C. (1985). Scand. J. Gastroenterol. 20 (Suppl. 117), 39–46.
3. Salt W. B. and Schenker S. (1976). Medicine 55: 269–289.
4. Temler R.S . and Felber J-P. (1976). Biochim. Biophys. Acta. 445: 720–728.
5. Elias E. et al (1977). Lancet ii: 66–68.
6. Borgstrom A. and Ohlsson K. (1978). Hoppe-Seyler's Z. Physiol. Chem. 359: 677–681.
7. Adrian T. E. et al (1979). Clin Chim Acta 97: 205–212.
8. Lake-Bakaar G. et al (1979). Lancet ii: 878–880.
9. Crossley J. R. et al (1979). Lancet i: 472–474.
10. Brodrick J. W. et al (1979) Am. J. Physiol. 237: E474–E480.
11. Geokas M. C. et al (1979). Am. J. Physiol. 236: E77–E83.
12. Koop H. et al (1980). Digestion 20: 151–156.
13. Duffy M. J. et al (1980). Clin. Chim. Acta. 103: 233–235.
14. Malvano R. et al (1980). Scand. J. Gastroenterol. 15(suppl. 62): 3–62.
15. Geokas M. C. et al (1981). Am. J. Pathol. 105: 31–39.
16. Farini R. et al (1981). Gastroenterology 81: 242–246.
17. Masoero G. et al (1982). Dig. Dis. Sci. 27: 1089–1094.
18. Steinberg W. M. and Anderson K. K. (1984). Dig. Dis. Sci. 29: 988–993.
19. Uxeki S. et al (1985). J. Lab. Clin. Med. 106: 578–582.
20. Wellborn J. C. et al (1983). Am. J. Surg. 146: 834–837.
21. Geokas M. C. et al (1979). J. Biol. Chem. 254: 2775–2781.
22. Eskola J. U. et al (1983). Clin. Chem. 29: 1777–1780.
23. Nevalainen T. J. et al (1985). Clin. Chem. 31: 1116–1120.
24. Delk A. S. et al (1985). Clin. Chem. 31: 1294–1300.
25. Goldberg J. M. (1976). Clin. Chem. 22: 638–642.
26. Mayer A. D. et al (1985). Br. J. Surg. 72: 436–437.
27. Kitahara T. et al (1980). Clin. Chim. Acta. 103: 135–143.
28. Otsuki M. et al (1984). Clin. Chim. Acta. 142: 231–240.
29. O'Connor C. M. et al (1981). Clin. Chim. Acta. 114: 29–35.
30. Hermon-Taylor J. et al (1981). Clin. Chim. Acta. 109: 203–209.
31. Massey T. H. (1985). Clin. Chem. 31: 70–75.
32. Pace B. W. et al (1985). Am. J. Gastroenterol. 80: 898–901.
33. Mifflin T. E. et al (1985). Clin. Chem. 31: 1283–1288.
34. Moller-Petersen J. et al (1986). Clin. Chim. Acta. 157: 151–166.
35. DiMagno E. P. (1983). Alabama J. Med. Sci. 20: 404–410.
36. Spechler S. J. et al (1983). Dig. Dis. Sci. 28: 865–869.
37. Eckfeldt J. H. et al (1985). Arch. Pathol. Lab. Med. 109: 316–319.
38. Puolakkainen P. et al (1987). Gut. 28: 764–771.
39. Traynor J. R. et al (1981). Biochim. Biophys. Acta. 665: 571–577.
40. Vadas P. (1984). J. Lab. Clin. Med. 104: 873–881.
41. Grataroli R. et al (1982). Eur. J. Biochem. 122: 111–117.
42. Sternby B. et al (1984). Biochim. Biophys. Acta. 786: 109–112.
43. Largman C. et al (1980). Biochim. Biophys. Acta. 623: 208–212.
44. Maroux S. et al (1971). J. Biol. Chem. 246: 5031–5039.
45. Broderick J. W. et al (1978). J. Biol. Chem. 253: 2737–2742.
46. Stanley C. J. et al (1985). J. Immunol. Methods 83: 89–95.
47. Carpino L. A. and Han G. Y. (1972). J. Org. Chem. 37: 3404–3409.
48. Wang S. (1973). J. Amer. Chem. Soc. 95: 1328–1333.
49. Meienhofer J. et al (1979). Int. J. Pep. Prot. Res. 13: 35–42.

50. Cliffe S. G. R. et al (1985). Int. J. Pep. Prot. Res. 25: 663–672.
51. Bassiri R. M. and Utiger R. D. (1972). Endocrinology 90: 722–727.
52. Green N. et al (1982). Cell 28: 477–484.
53. Hoffman W. et al EMBO. J. (1983). 2: 711–714.
54. Cawthorne S. J. et al (1984). Dig. Dis. Sci. 29: 945.
55. Shorrock K. et al (1986). Gut 27: A1260.
56. Ranson J. H. C. et al (1974). S. G.0. 139: 69–81.
57. Sternby B. et al (1984). Biochim. Biophys. Acta. 789: 164–69.
58. Vadas P. and Hay J. B. (1980). Life Sci. 26: 1721–29.
59. Lanni C. et al (1981). Biochim. Biophys. Act. 658: 54–63.
60. Lanni C. et al (1983). Am. J. Pathol. 113: 90–94.
61. Franson R. C. et al (1973). J. Cell. Biol. 56: 621–627.
62. Franson R. C. et al (1978). J. Lipid. Res. 19: 18–23.
63. Vadas P. (1984). J. Lab. Clin. Med. 104: 873–881.

We claim:

1. A method of diagnosing pancreatic disease in a patient which comprises assaying a sample of the patient's body fluid for the presence or absence of peptides which are the activation peptides of pancreatic zymogens specifically cleaved by proteolysis during activation (PAP), the pancreatic zymogen being selected from the group consisting of trypsinogen, prophospholipase $A_2$, procolipase, proelastase 1, proelastase 2, prekallekrein, procarboxypeptidases A, and procarboxypeptidases B, the activation peptide being selected from the group consisting of trypsinogen activation peptide (TAP), prophospholipase $A_2$ activation peptide (PLAP), procolipase activation peptide (CLAP), proelastase 1 activation peptide, proelastae 2 activation peptide (PEAP), perkallekrein activation peptide, procarboxypeptidases A activation peptide and procarboxypeptidases B activation peptide, 2. A method according to claim 1 wherein the peptide assayed for is a trypsinogen activation peptide (TAP) comprising the amino acid sequence $D_4K$ having the lysine (K) as the carboxy terminus.

3. A method according to claim 1 wherein the peptide assayed for is human pancreatic prophospholipase A2 activation peptide (PLAP) comprising the amino acid sequence

D S G I S P R having the R as the carboxy terminus,
or procolipase activation peptide (CLAP) comprising the amino acid sequence

A P G P R having the R as the carboxy terminus
or proelastase 2 activation peptide (PEAP) comprising the amino acid sequence

G D P T Y P P Y V T R having the R as the carboxy terminus or the degradation product of proelastase 2 activation peptide (PEAP) comprising the amino acid sequence

P P Y V T R having the R as the carboxy terminus.

4. A method according to claim 1 wherein the body fluid is blood serum, ascites or urine.

5. A method according to claim 1 wherein the antibody has specificity for TAP, PLAP, CLAP or PEAP.

6. A method according to claim 5 involving the formation of a conjugate between the PAP and the corresponding antibody, said conjugate carrying a revealing label and being formed either in the solid phase or in the liquid phase of a solid/liquid phase reaction mixture, separating the solid phase from the liquid phase and determining the presence of or amount of the revealing label in either the solid phase or the liquid phase as a measure of the presence of or amount of, respectively, PAP in the sample.

7. A method according to claim 6 carried out as an ELISA or using biotin labelled antibody.

8. A method according to claim 6 carried out as an ELISA or using biotin labelled PAP.

9. A process according to claim 1 wherein the sample is brought into contact with a solid phase comprising an inert solid support to which is bound either (1) PAP having a corresponding antibody bound thereto, the antibody carrying a revealing label, or (2) a corresponding antibody to PAP having PAP bound thereto, the PAP carrying a revealing label.

10. A method according to claim 1 wherein samples of body fluid are removed from the patient on at least two separate occasions spaced apart from one another by at least 2 hours and each sample is assayed for the concentration of PAP as a means for monitoring the severity progress of pancreatitis.

* * * * *